(12) United States Patent
Andersen et al.

(10) Patent No.: US 9,163,077 B2
(45) Date of Patent: Oct. 20, 2015

(54) RHOC-BASED IMMUNOTHERAPY

(75) Inventors: Mads Hald Andersen, Nærum (DK);
Per Thor Straten, Hvidovre (DK)

(73) Assignee: RHOVAC APS, Horsholm (DK)

( * ) Notice: Subject to any disclaimer, the term of this patent is extended or adjusted under 35 U.S.C. 154(b) by 1180 days.

(21) Appl. No.: 12/808,649

(22) PCT Filed: Dec. 18, 2008

(86) PCT No.: PCT/DK2008/050324
§ 371 (c)(1),
(2), (4) Date: Sep. 23, 2010

(87) PCT Pub. No.: WO2009/076966
PCT Pub. Date: Jun. 25, 2009

(65) Prior Publication Data
US 2011/0002954 A1    Jan. 6, 2011

(30) Foreign Application Priority Data
Dec. 19, 2007 (DK) .............................. 2007 01844

(51) Int. Cl.
| A61K 39/00 | (2006.01) |
|---|---|
| A61K 35/12 | (2015.01) |
| A61P 35/00 | (2006.01) |
| A61P 35/04 | (2006.01) |
| C07K 14/82 | (2006.01) |
| C07K 14/47 | (2006.01) |
| A61K 38/00 | (2006.01) |

(52) U.S. Cl.
CPC ............. *C07K 14/82* (2013.01); *C07K 14/4702* (2013.01); *A61K 38/00* (2013.01)

(58) Field of Classification Search
None
See application file for complete search history.

(56) References Cited

U.S. PATENT DOCUMENTS

| 7,960,100 B1 * | 6/2011 | Domon et al. .................... 435/4 |
|---|---|---|
| 2001/0044414 A1 | 11/2001 | Clark et al. |
| 2003/0039635 A1 * | 2/2003 | Gaiger et al. ................ 424/93.2 |

FOREIGN PATENT DOCUMENTS

| DE | 102 17 035 | 1/2004 | |
|---|---|---|---|
| JP | 2005-509404 | 4/2005 | |
| WO | WO 99/33870 | 7/1999 | |
| WO | WO 99/62932 | 12/1999 | |
| WO | WO02/34771 | * | 5/2002 |
| WO | WO03/040165 | * | 5/2003 |
| WO | WO2005/017160 | * | 8/2004 |
| WO | WO2007/005946 | * | 7/2006 |

OTHER PUBLICATIONS

Novellino et al (Cancer Immunology Immunotherapy, 2005, vol. 54, pp. 187-207).*
Wheeler (Salud p'ublica de M'exico, (1997, vol. 39, pp. 283-287).*
Efferson et al (Anticancer research, 2005, vol. 25, pp. 715-724).*
Bachman et al (Journal of Immunology, 2005, vol. 175, pp. 4677-4685).*
Trefzer et al, Molecular Biotechnology, 2003. vol. 25, pp. 63-69.*
International Search Report from International Application No. PCT/DK2008/050324 mailed Jun. 29, 2009 (Form PCT/ISA/210).
Abecassis et al. (Dec. 15, 2003): "RhoA induces MMP-9 expression at CD44 lamellipodial focal complexes and promotes HMEC-1 cell invasion" *Exp Cell Res*, vol. 291, No. 2, pp. 363-376.
Allal C et al (Oct. 6, 2000): "RhoA prenylation is required for promotion of cell growth and transformation and cytoskeleton organization but not for induction of serum response element transcription" *J Biol Chem*, vol. 275, No. 40, pp. 3100-3108.
Andersen MH et al (Oct. 1, 1999): "Phosphorylated peptides can be transported by TAP molecules, presented by class I MHC molecules, and recognized by phosphopeptide-specific CTL" *J Immunol*, vol. 163, No. 7, pp. 3812-3818.
Barnstable CJ et al. (1978): "Production of monoclonal antibodies to group-A erythrocytes" *Cell*, vol. 14, pp. 9-20.
Bishop AL et al (Jun. 1, 2000): Rho GTPases and their effector proteins: *Biochem J*, vol. 348, pt. 2, pp. 241-255.
Clark EA et al. (Aug. 3, 2000): "Genomic analysis of metastasis reveals an essential role for RhoC" *Nature*, vol. 406, No. 6795, pp. 532-535.
Hakem A et al. (2005): "RhoC is dispensible for embryogenesis and tumor initiation but essential for metastasis" *Genes & Development*, vol. 19, No. 17, pp. 1974-1979.
Horiuchi A et al. (Jun. 2003): "Up-regulation of small GTPases, RhoA and RhoC, is associated with tumor progression in ovarian carcinoma " *Lab Invest*, vol. 83, No. 6, pp. 861-870.
Kirkin AF et al. (Aug. 1995): "Generation of human-melanoma-specific T lymphocyte clones defining novel cytolytic targets with panels of newly established melanoma cell lines" *Cancer Immunology, Immunotherapy: CII*, vol. 41, No. 2, pp. 71-81.
Kleer CG et al. (2006): "RhoC GTPase expression as a potential marker of lymph node metestasis in squamous cell carcinomas in the head and neck" *Clinical cancer research: an official journal of the American association for cancer research*, vol. 12, No. 15, pp. 4485-4490.
Kleer CG et al. (Feb. 2002): "Characterization of RhoC expression in benign and malignant breast disease: a potential new marker for small breast carcinomas with metastatic ability" *Am J Pathol*, vol. 160, No. 2, pp. 579-584.
Liu et al (2007): "RhoC is essential for the metastasis of gastric cancer" *Journal of molecular medicine*, vol. 85, No. 10, pp. 1149-1156.

(Continued)

*Primary Examiner* — Karen Canella
(74) *Attorney, Agent, or Firm* — Merchant & Gould, P.C.

(57) ABSTRACT

The present invention relates generally to the field of prophylaxis and therapy of metastatic cancer. In particular there is provided a protein; Ras Homology gene family, member C (RhoC) or peptide fragments thereof that are capable of eliciting anti-cancer immune responses. Specifically, the invention relates to use of RhoC or peptides derived thereof or RhoC specific T-cells for treatment of metastatic cancer. Hence, the invention in one aspect relates to RhoC specific T-cells adoptively transferred or induced in vivo by vaccination as a treatment of cancer. Also the use of RhoC and immunogenic peptide fragments hereof in cancer treatment, diagnosis and prognosis is provided.

15 Claims, 5 Drawing Sheets

(56) References Cited

OTHER PUBLICATIONS

Morgan RA et al. (Oct. 6, 2006): "Cancer regression in patients after transfer of genetically engineered lymphocytes" *Science* vol. 314-, No. 5796, pp. 126-129.

Nicolette CA et al (Sep. 27, 2007): "Dendritic cells for active immunotherapy: optimizing design and manufacture in order to develop commercially and clinically viable products" *Vaccine*, vol. 25, suppl. 2:B, pp. 47-60.

Pardoll DM (1998): "Cancer Vaccines" *Nat med*, vol. 4, pp. 525-531.

Ridley AJ (2004): "Rho proteins and cancer" *Breast cancer research and treatment* vol. 84, No. 1, pp. 13-19.

Rosenberg SA et al. (1998): "Immunologic and therapeutic evaluation of a synthetic peptide vaccine for the treatment of patients with metastatic melanoma" *Nature Medicine*, vol. 4, No. 3, pp. 321-327.

Scheibenbogen C et al. (2002): "Identification of known and novel immunogenic T-cell epitopes from tumor antigens recognized by peripheral blood T-cells from patients responding to IL-based treatment" Int J Cancer, vol. 98, pp. 409-414.

Schmidt SM et al (2003): "Survivin is a shared tumor-associated antigen expressed in a borad variety of malignancies and recognized by specific cytotoxic T cells" *Blood*, vol. 102, pp. 571-576.

Shao F et al. (2003): "YopT is a cysteine protease cleaving Rho family GTPases" *Adv Exp Med Biol*, vol. 529, pp. 79-84.

Simpson K J et al (2004): "Functional Analysis of the Contribution of RhoA and RhoC GTPases to Invasive Breast Carcinoma" *Cancer Research* 64, 8694-8701.

Sire J et al. (1988):"Hybrid genes between HLA-A2 and HLA-A3 constructed by in vivo recombination allow mapping of HLA-A2 and HLA-A3 polymorphic antigenic determinants." J Immunol, vol. 140, No. 7, pp. 2422-2430.

Stamatakis K et al. (2002): "Isoprenylation of RhoB is necessary for its degradation. A novel determinant in the complex regulation of RhoB expression by the mevalonate pathway." *J Biol Chem*, vol. 277, No. 51, pp. 49389-49396.

Walter EA et al. (1995): "Reconstitution of cellular immunity against cytomegalovirus in recipients of allogeneic bone marrow by transfer of T-cell clones from the donor" *N Engl J Med*, vol. 333, No. 16, pp. 1038-1044.

Wenandy L et al. (2008): "RhoC a new target for therapeutic vaccination against metastatic cancer." *Cancer Immunology*, Immunotherapy, vol. 57, No. 12, pp. 1871-1878.

Wennerberg K et al (2004): "Rho-family GTPases: it's not only Rac and Rho (and I like it)." *J of Cell Science* 117, pp. 1301-1312.

Wu et al. (2004): "RhoC induces differential expression of genes involved in invasion and metastasis in MCF10A breast cells." *Breast cancer research and treatment*, vol. 84, No. 1, pp. 3-12.

Peter Adamson et al; "Intracellular Localization of the p21rho Proteins"; Journ Cell Bio, vol. 119(3), pp. 617-623; 1992.

\* cited by examiner

Fig. 1

```
CLUSTAL W (1.83) multiple sequence alignment

P61586|RHOA_HUMAN       MAAIRKKLVIVGDACGKTCLLIVFSKDQFPEVYVPTVFENYVADIEVDGKQVELALWDT 60
P08134|RHOC_HUMAN       MAAIRKKLVIVGDACGKTCLLIVFSKDQFPEVYVPTVFENYIADIEVDGKQVELALWDT 60
P62745|RHOB_HUMAN       MAAIRKKLVVVGDACGKTCLLIVFSKDEFPEVYVPTVFENYVADIEVDGKQVELALWDT 60
                        *********:*****************:***********:*****************

P61586|RHOA_HUMAN       AGQEDYDRLRPLSYPDTDVILMCFSIDSPDSLENIPEKWTPEVKHFCPNVPIILVGNKKD 120
P08134|RHOC_HUMAN       AGQEDYDRLRPLSYPDTDVILMCFSIDSPDSLENIPEKWTPEVKHFCPNVPIILVGNKKD 120
P62745|RHOB_HUMAN       AGQEDYDRLRPLSYPDTDVILMCFSVDSPDSLENIPEKWVPEVKHFCPNVPIILVANKKD 120
                        ************************:**************.***************.****

P61586|RHOA_HUMAN       LRNDEHTRRELAKMKQEPVKPEEGRDMANRIGAFGYMECSAKTKDGVREVFEMATRAALQ 180
P08134|RHOC_HUMAN       LRQDEHTRRELAKMKQEPVRSEEGRDMANRISAFGYLECSAKTKEGVREVFEMATRAGLQ 180
P62745|RHOB_HUMAN       LRSDEHVRTELARMKQEPVRTDDGRAMAVRIQAYDYLECSAKTKEGVREVFETATRAALQ 180
                        **.***.* ***:******:..:** ** ** *:.*:*******:******* ****.**

P61586|RHOA_HUMAN       ARRGKKK---SGCLVL 193
P08134|RHOC_HUMAN       VRKNKRR---RGCPIL 193
P62745|RHOB_HUMAN       KRYGSQNGCINCCKVL 196
                        *  ..:.    *  :*
```

Fig. 5
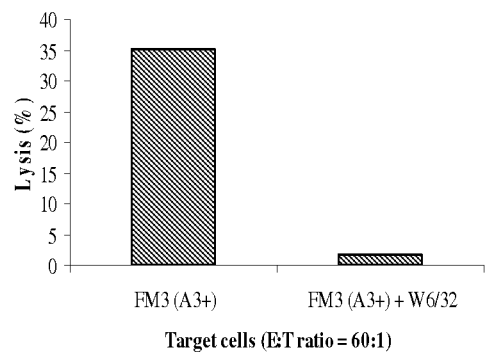
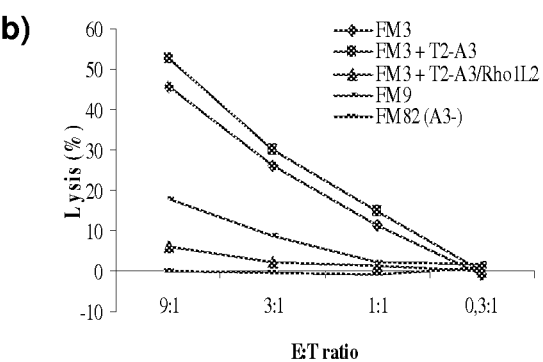
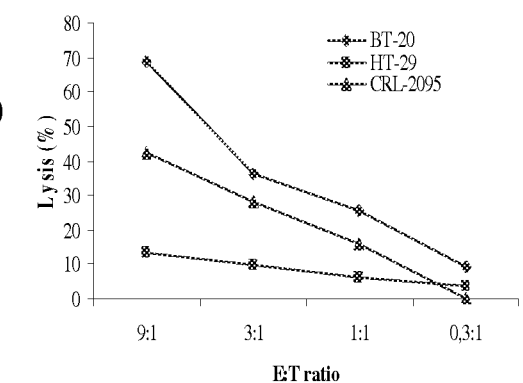

SEQUENCE LISTING

```
<160> NUMBER OF SEQ ID NOS: 178

<210> SEQ ID NO 1
<211> LENGTH: 193
<212> TYPE: PRT
<213> ORGANISM: Homo sapiens

<400> SEQUENCE: 1

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Ile Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Gln Asp Glu His Thr Arg
        115                 120                 125

Arg Glu Leu Ala Lys Met Lys Gln Glu Pro Val Arg Ser Glu Glu Gly
    130                 135                 140

Arg Asp Met Ala Asn Arg Ile Ser Ala Phe Gly Tyr Leu Glu Cys Ser
145                 150                 155                 160

Ala Lys Thr Lys Glu Gly Val Arg Glu Val Phe Glu Met Ala Thr Arg
                165                 170                 175

Ala Gly Leu Gln Val Arg Lys Asn Lys Arg Arg Arg Gly Cys Pro Ile
            180                 185                 190

Leu

<210> SEQ ID NO 2
<211> LENGTH: 193
<212> TYPE: PRT
<213> ORGANISM: Homo sapiens
```

<400> SEQUENCE: 2

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 3
<211> LENGTH: 196
<212> TYPE: PRT
<213> ORGANISM: Homo sapiens

<400> SEQUENCE: 3

Met Ala Ala Ile Arg Lys Lys Leu Val Val Gly Asp Gly Ala Cys
1               5                   10                  15

Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Val Asp Ser Pro Asp Ser Leu Glu Asn Ile Pro
                85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
        115                 120                 125

Thr Glu Leu Ala Arg Met Lys Gln Glu Pro Val Arg Thr Asp Asp Gly
    130                 135                 140

Arg Ala Met Ala Val Arg Ile Gln Ala Tyr Asp Tyr Leu Glu Cys Ser
145                 150                 155                 160

```
Ala Lys Thr Lys Glu Gly Val Arg Glu Val Phe Glu Thr Ala Thr Arg
                165                 170                 175

Ala Ala Leu Gln Lys Arg Tyr Gly Ser Gln Asn Gly Cys Ile Asn Cys
            180                 185                 190

Cys Lys Val Leu
        195

<210> SEQ ID NO 4
<211> LENGTH: 20
<212> TYPE: PRT
<213> ORGANISM: Homo sapiens

<400> SEQUENCE: 4

Ala Thr Arg Ala Gly Leu Gln Val Arg Lys Asn Lys Arg Arg Arg Gly
1               5                   10                  15

Cys Pro Ile Leu
            20

<210> SEQ ID NO 5
<211> LENGTH: 21
<212> TYPE: PRT
<213> ORGANISM: Homo sapiens

<400> SEQUENCE: 5

Val Tyr Val Pro Thr Val Phe Glu Asn Tyr Ile Ala Asp Ile Glu Val
1               5                   10                  15

Asp Gly Lys Gln Val
            20

<210> SEQ ID NO 6
<211> LENGTH: 19
<212> TYPE: PRT
<213> ORGANISM: Homo sapiens

<400> SEQUENCE: 6

Ile Leu Val Gly Asn Lys Lys Leu Arg Gln Asp Glu His Thr Arg Arg
1               5                   10                  15

Leu Ala Lys

<210> SEQ ID NO 7
<211> LENGTH: 21
<212> TYPE: PRT
<213> ORGANISM: Homo sapiens

<400> SEQUENCE: 7

Glu Leu Ala Lys Met Lys Gln Glu Pro Val Arg Ser Glu Glu Gly Arg
1               5                   10                  15

Asp Met Ala Asn Arg
            20

<210> SEQ ID NO 8
<211> LENGTH: 52
<212> TYPE: PRT
<213> ORGANISM: Homo sapiens

<400> SEQUENCE: 8

Glu Glu Gly Arg Asp Met Ala Asn Arg Ile Ser Ala Phe Gly Tyr Lys
1               5                   10                  15

Glu Cys Ser Ala Lys Thr Lys Glu Gly Val Arg Glu Val Phe Glu Met
            20                  25                  30

Ala Thr Arg Ala Gly Leu Gln Val Arg Lys Asn Lys Arg Arg Arg Gly
```

```
                  35                  40                  45
Cys Pro Ile Leu
    50

<210> SEQ ID NO 9
<211> LENGTH: 10
<212> TYPE: PRT
<213> ORGANISM: Artificial
<220> FEATURE:
<223> OTHER INFORMATION: Subsitution of A to L from human RhoC sequence
      RAGLQVRKNK

<400> SEQUENCE: 9

Arg Leu Gly Leu Gln Val Arg Lys Asn Lys
1               5                   10

<210> SEQ ID NO 10
<211> LENGTH: 10
<212> TYPE: PRT
<213> ORGANISM: Homo sapiens

<400> SEQUENCE: 10

Arg Ala Gly Leu Gln Val Arg Lys Asn Lys
1               5                   10

<210> SEQ ID NO 11
<211> LENGTH: 9
<212> TYPE: PRT
<213> ORGANISM: Homo sapiens

<400> SEQUENCE: 11

Ala Thr Arg Ala Gly Leu Gln Val Arg
1               5

<210> SEQ ID NO 12
<211> LENGTH: 9
<212> TYPE: PRT
<213> ORGANISM: Homo sapiens

<400> SEQUENCE: 12

Thr Arg Ala Gly Leu Gln Val Arg Lys
1               5

<210> SEQ ID NO 13
<211> LENGTH: 9
<212> TYPE: PRT
<213> ORGANISM: Homo sapiens

<400> SEQUENCE: 13

Arg Ala Gly Leu Gln Val Arg Lys Asn
1               5

<210> SEQ ID NO 14
<211> LENGTH: 9
<212> TYPE: PRT
<213> ORGANISM: Homo sapiens

<400> SEQUENCE: 14

Ala Gly Leu Gln Val Arg Lys Asn Lys
1               5

<210> SEQ ID NO 15
<211> LENGTH: 9
<212> TYPE: PRT
<213> ORGANISM: Homo sapiens
```

<400> SEQUENCE: 15

Gly Leu Gln Val Arg Lys Asn Lys Arg
1               5

<210> SEQ ID NO 16
<211> LENGTH: 9
<212> TYPE: PRT
<213> ORGANISM: Homo sapiens

<400> SEQUENCE: 16

Leu Gln Val Arg Lys Asn Lys Arg Arg
1               5

<210> SEQ ID NO 17
<211> LENGTH: 9
<212> TYPE: PRT
<213> ORGANISM: Homo sapiens

<400> SEQUENCE: 17

Gln Val Arg Lys Asn Lys Arg Arg Arg
1               5

<210> SEQ ID NO 18
<211> LENGTH: 9
<212> TYPE: PRT
<213> ORGANISM: Homo sapiens

<400> SEQUENCE: 18

Val Arg Lys Asn Lys Arg Arg Arg Gly
1               5

<210> SEQ ID NO 19
<211> LENGTH: 9
<212> TYPE: PRT
<213> ORGANISM: Homo sapiens

<400> SEQUENCE: 19

Arg Lys Asn Lys Arg Arg Arg Gly Cys
1               5

<210> SEQ ID NO 20
<211> LENGTH: 9
<212> TYPE: PRT
<213> ORGANISM: Homo sapiens

<400> SEQUENCE: 20

Lys Asn Lys Arg Arg Arg Gly Cys Pro
1               5

<210> SEQ ID NO 21
<211> LENGTH: 9
<212> TYPE: PRT
<213> ORGANISM: Homo sapiens

<400> SEQUENCE: 21

Asn Lys Arg Arg Arg Gly Cys Pro Ile
1               5

<210> SEQ ID NO 22
<211> LENGTH: 9
<212> TYPE: PRT
<213> ORGANISM: Homo sapiens

<400> SEQUENCE: 22

```
Lys Arg Arg Arg Gly Cys Pro Ile Leu
1               5
```

<210> SEQ ID NO 23
<211> LENGTH: 10
<212> TYPE: PRT
<213> ORGANISM: Homo sapiens

<400> SEQUENCE: 23

```
Ala Thr Arg Ala Gly Leu Gln Val Arg Lys
1               5                   10
```

<210> SEQ ID NO 24
<211> LENGTH: 10
<212> TYPE: PRT
<213> ORGANISM: Homo sapiens

<400> SEQUENCE: 24

```
Thr Arg Ala Gly Leu Gln Val Arg Lys Asn
1               5                   10
```

<210> SEQ ID NO 25
<211> LENGTH: 10
<212> TYPE: PRT
<213> ORGANISM: Homo sapiens

<400> SEQUENCE: 25

```
Arg Ala Gly Leu Gln Val Arg Lys Asn Lys
1               5                   10
```

<210> SEQ ID NO 26
<211> LENGTH: 10
<212> TYPE: PRT
<213> ORGANISM: Homo sapiens

<400> SEQUENCE: 26

```
Ala Gly Leu Gln Val Arg Lys Asn Lys Arg
1               5                   10
```

<210> SEQ ID NO 27
<211> LENGTH: 10
<212> TYPE: PRT
<213> ORGANISM: Homo sapiens

<400> SEQUENCE: 27

```
Gly Leu Gln Val Arg Lys Asn Lys Arg Arg
1               5                   10
```

<210> SEQ ID NO 28
<211> LENGTH: 10
<212> TYPE: PRT
<213> ORGANISM: Homo sapiens

<400> SEQUENCE: 28

```
Leu Gln Val Arg Lys Asn Lys Arg Arg Arg
1               5                   10
```

<210> SEQ ID NO 29
<211> LENGTH: 10
<212> TYPE: PRT
<213> ORGANISM: Homo sapiens

<400> SEQUENCE: 29

```
Gln Val Arg Lys Asn Lys Arg Arg Arg Gly
```

```
1               5                   10
```

<210> SEQ ID NO 30
<211> LENGTH: 10
<212> TYPE: PRT
<213> ORGANISM: Homo sapiens

<400> SEQUENCE: 30

```
Val Arg Lys Asn Lys Arg Arg Arg Gly Cys
1               5                   10
```

<210> SEQ ID NO 31
<211> LENGTH: 10
<212> TYPE: PRT
<213> ORGANISM: Homo sapiens

<400> SEQUENCE: 31

```
Arg Lys Asn Lys Arg Arg Arg Gly Cys Pro
1               5                   10
```

<210> SEQ ID NO 32
<211> LENGTH: 10
<212> TYPE: PRT
<213> ORGANISM: Homo sapiens

<400> SEQUENCE: 32

```
Lys Asn Lys Arg Arg Arg Gly Cys Pro Ile
1               5                   10
```

<210> SEQ ID NO 33
<211> LENGTH: 10
<212> TYPE: PRT
<213> ORGANISM: Homo sapiens

<400> SEQUENCE: 33

```
Asn Lys Arg Arg Arg Gly Cys Pro Ile Leu
1               5                   10
```

<210> SEQ ID NO 34
<211> LENGTH: 10
<212> TYPE: PRT
<213> ORGANISM: Homo sapiens

<400> SEQUENCE: 34

```
Tyr Val Pro Thr Val Phe Glu Asn Tyr Ile
1               5                   10
```

<210> SEQ ID NO 35
<211> LENGTH: 10
<212> TYPE: PRT
<213> ORGANISM: Homo sapiens

<400> SEQUENCE: 35

```
Val Pro Thr Val Phe Glu Asn Tyr Ile Ala
1               5                   10
```

<210> SEQ ID NO 36
<211> LENGTH: 10
<212> TYPE: PRT
<213> ORGANISM: Homo sapiens

<400> SEQUENCE: 36

```
Pro Thr Val Phe Glu Asn Tyr Ile Ala Asp
1               5                   10
```

```
<210> SEQ ID NO 37
<211> LENGTH: 10
<212> TYPE: PRT
<213> ORGANISM: Homo sapiens

<400> SEQUENCE: 37

Thr Val Phe Glu Asn Tyr Ile Ala Asp Ile
1               5                   10

<210> SEQ ID NO 38
<211> LENGTH: 10
<212> TYPE: PRT
<213> ORGANISM: Homo sapiens

<400> SEQUENCE: 38

Val Phe Glu Asn Tyr Ile Ala Asp Ile Glu
1               5                   10

<210> SEQ ID NO 39
<211> LENGTH: 10
<212> TYPE: PRT
<213> ORGANISM: Homo sapiens

<400> SEQUENCE: 39

Phe Glu Asn Tyr Ile Ala Asp Ile Glu Val
1               5                   10

<210> SEQ ID NO 40
<211> LENGTH: 10
<212> TYPE: PRT
<213> ORGANISM: Homo sapiens

<400> SEQUENCE: 40

Glu Asn Tyr Ile Ala Asp Ile Glu Val Asp
1               5                   10

<210> SEQ ID NO 41
<211> LENGTH: 10
<212> TYPE: PRT
<213> ORGANISM: Homo sapiens

<400> SEQUENCE: 41

Asn Tyr Ile Ala Asp Ile Glu Val Asp Gly
1               5                   10

<210> SEQ ID NO 42
<211> LENGTH: 10
<212> TYPE: PRT
<213> ORGANISM: Homo sapiens

<400> SEQUENCE: 42

Tyr Ile Ala Asp Ile Glu Val Asp Gly Lys
1               5                   10

<210> SEQ ID NO 43
<211> LENGTH: 10
<212> TYPE: PRT
<213> ORGANISM: Homo sapiens

<400> SEQUENCE: 43

Ile Ala Asp Ile Glu Val Asp Gly Lys Gln
1               5                   10

<210> SEQ ID NO 44
```

```
<211> LENGTH: 10
<212> TYPE: PRT
<213> ORGANISM: Homo sapiens

<400> SEQUENCE: 44

Leu Val Gly Asn Lys Lys Asp Leu Arg Gln
1               5                   10

<210> SEQ ID NO 45
<211> LENGTH: 10
<212> TYPE: PRT
<213> ORGANISM: Homo sapiens

<400> SEQUENCE: 45

Val Gly Asn Lys Lys Asp Leu Arg Gln Asp
1               5                   10

<210> SEQ ID NO 46
<211> LENGTH: 10
<212> TYPE: PRT
<213> ORGANISM: Homo sapiens

<400> SEQUENCE: 46

Gly Asn Lys Lys Asp Leu Arg Gln Asp Glu
1               5                   10

<210> SEQ ID NO 47
<211> LENGTH: 10
<212> TYPE: PRT
<213> ORGANISM: Homo sapiens

<400> SEQUENCE: 47

Asn Lys Lys Asp Leu Arg Gln Asp Glu His
1               5                   10

<210> SEQ ID NO 48
<211> LENGTH: 10
<212> TYPE: PRT
<213> ORGANISM: Homo sapiens

<400> SEQUENCE: 48

Lys Lys Asp Leu Arg Gln Asp Glu His Thr
1               5                   10

<210> SEQ ID NO 49
<211> LENGTH: 9
<212> TYPE: PRT
<213> ORGANISM: Homo sapiens

<400> SEQUENCE: 49

Lys Leu Arg Gln Asp Glu His Thr Arg
1               5

<210> SEQ ID NO 50
<211> LENGTH: 10
<212> TYPE: PRT
<213> ORGANISM: Homo sapiens

<400> SEQUENCE: 50

Lys Leu Arg Gln Asp Glu His Thr Arg Arg
1               5                   10

<210> SEQ ID NO 51
<211> LENGTH: 10
<212> TYPE: PRT
```

<213> ORGANISM: Homo sapiens

<400> SEQUENCE: 51

Leu Arg Gln Asp Glu His Thr Arg Arg Glu
1               5                   10

<210> SEQ ID NO 52
<211> LENGTH: 9
<212> TYPE: PRT
<213> ORGANISM: Homo sapiens

<400> SEQUENCE: 52

Gln Asp Glu His Thr Arg Arg Glu Leu
1               5

<210> SEQ ID NO 53
<211> LENGTH: 9
<212> TYPE: PRT
<213> ORGANISM: Homo sapiens

<400> SEQUENCE: 53

Asp Glu His Thr Arg Arg Glu Leu Ala
1               5

<210> SEQ ID NO 54
<211> LENGTH: 10
<212> TYPE: PRT
<213> ORGANISM: Homo sapiens

<400> SEQUENCE: 54

Leu Ala Lys Met Lys Gln Glu Pro Val Arg
1               5                   10

<210> SEQ ID NO 55
<211> LENGTH: 10
<212> TYPE: PRT
<213> ORGANISM: Homo sapiens

<400> SEQUENCE: 55

Ala Lys Met Lys Gln Glu Pro Val Arg Ser
1               5                   10

<210> SEQ ID NO 56
<211> LENGTH: 10
<212> TYPE: PRT
<213> ORGANISM: Homo sapiens

<400> SEQUENCE: 56

Lys Met Lys Gln Glu Pro Val Arg Ser Glu
1               5                   10

<210> SEQ ID NO 57
<211> LENGTH: 10
<212> TYPE: PRT
<213> ORGANISM: Homo sapiens

<400> SEQUENCE: 57

Met Lys Gln Glu Pro Val Arg Ser Glu Glu
1               5                   10

<210> SEQ ID NO 58
<211> LENGTH: 10
<212> TYPE: PRT
<213> ORGANISM: Homo sapiens

<400> SEQUENCE: 58

Lys Gln Glu Pro Val Arg Ser Glu Glu Gly
1               5                   10

<210> SEQ ID NO 59
<211> LENGTH: 10
<212> TYPE: PRT
<213> ORGANISM: Homo sapiens

<400> SEQUENCE: 59

Gln Glu Pro Val Arg Ser Glu Glu Gly Arg
1               5                   10

<210> SEQ ID NO 60
<211> LENGTH: 10
<212> TYPE: PRT
<213> ORGANISM: Homo sapiens

<400> SEQUENCE: 60

Glu Pro Val Arg Ser Glu Glu Gly Arg Asp
1               5                   10

<210> SEQ ID NO 61
<211> LENGTH: 10
<212> TYPE: PRT
<213> ORGANISM: Homo sapiens

<400> SEQUENCE: 61

Pro Val Arg Ser Glu Glu Gly Arg Asp Met
1               5                   10

<210> SEQ ID NO 62
<211> LENGTH: 10
<212> TYPE: PRT
<213> ORGANISM: Homo sapiens

<400> SEQUENCE: 62

Val Arg Ser Glu Glu Gly Arg Asp Met Ala
1               5                   10

<210> SEQ ID NO 63
<211> LENGTH: 10
<212> TYPE: PRT
<213> ORGANISM: Homo sapiens

<400> SEQUENCE: 63

Arg Ser Glu Glu Gly Arg Asp Met Ala Asn
1               5                   10

<210> SEQ ID NO 64
<211> LENGTH: 10
<212> TYPE: PRT
<213> ORGANISM: Homo sapiens

<400> SEQUENCE: 64

Ser Glu Glu Gly Arg Asp Met Ala Asn Arg
1               5                   10

<210> SEQ ID NO 65
<211> LENGTH: 10
<212> TYPE: PRT
<213> ORGANISM: Homo sapiens

<400> SEQUENCE: 65

Glu Gly Arg Asp Met Ala Asn Arg Ile Ser
1               5                   10

<210> SEQ ID NO 66
<211> LENGTH: 10
<212> TYPE: PRT
<213> ORGANISM: Homo sapiens

<400> SEQUENCE: 66

Gly Arg Asp Met Ala Asn Arg Ile Ser Ala
1               5                   10

<210> SEQ ID NO 67
<211> LENGTH: 10
<212> TYPE: PRT
<213> ORGANISM: Homo sapiens

<400> SEQUENCE: 67

Arg Asp Met Ala Asn Arg Ile Ser Ala Phe
1               5                   10

<210> SEQ ID NO 68
<211> LENGTH: 10
<212> TYPE: PRT
<213> ORGANISM: Homo sapiens

<400> SEQUENCE: 68

Asp Met Ala Asn Arg Ile Ser Ala Phe Gly
1               5                   10

<210> SEQ ID NO 69
<211> LENGTH: 10
<212> TYPE: PRT
<213> ORGANISM: Homo sapiens

<400> SEQUENCE: 69

Met Ala Asn Arg Ile Ser Ala Phe Gly Tyr
1               5                   10

<210> SEQ ID NO 70
<211> LENGTH: 9
<212> TYPE: PRT
<213> ORGANISM: Homo sapiens

<400> SEQUENCE: 70

Asn Arg Ile Ser Ala Phe Gly Tyr Leu
1               5

<210> SEQ ID NO 71
<211> LENGTH: 10
<212> TYPE: PRT
<213> ORGANISM: Homo sapiens

<400> SEQUENCE: 71

Asn Arg Ile Ser Ala Phe Gly Tyr Leu Glu
1               5                   10

<210> SEQ ID NO 72
<211> LENGTH: 9
<212> TYPE: PRT
<213> ORGANISM: Homo sapiens

<400> SEQUENCE: 72

Ile Ser Ala Phe Gly Tyr Leu Glu Cys
1               5

<210> SEQ ID NO 73
<211> LENGTH: 10
<212> TYPE: PRT
<213> ORGANISM: Homo sapiens

<400> SEQUENCE: 73

Ile Ser Ala Phe Gly Tyr Leu Glu Cys Ser
1               5                   10

<210> SEQ ID NO 74
<211> LENGTH: 9
<212> TYPE: PRT
<213> ORGANISM: Homo sapiens

<400> SEQUENCE: 74

Ala Phe Gly Tyr Leu Glu Cys Ser Ala
1               5

<210> SEQ ID NO 75
<211> LENGTH: 10
<212> TYPE: PRT
<213> ORGANISM: Homo sapiens

<400> SEQUENCE: 75

Ala Phe Gly Tyr Leu Glu Cys Ser Ala Lys
1               5                   10

<210> SEQ ID NO 76
<211> LENGTH: 10
<212> TYPE: PRT
<213> ORGANISM: Homo sapiens

<400> SEQUENCE: 76

Phe Gly Tyr Leu Glu Cys Ser Ala Lys Thr
1               5                   10

<210> SEQ ID NO 77
<211> LENGTH: 10
<212> TYPE: PRT
<213> ORGANISM: Homo sapiens

<400> SEQUENCE: 77

Gly Tyr Leu Glu Cys Ser Ala Lys Thr Lys
1               5                   10

<210> SEQ ID NO 78
<211> LENGTH: 10
<212> TYPE: PRT
<213> ORGANISM: Homo sapiens

<400> SEQUENCE: 78

Tyr Leu Glu Cys Ser Ala Lys Thr Lys Glu
1               5                   10

<210> SEQ ID NO 79
<211> LENGTH: 10
<212> TYPE: PRT
<213> ORGANISM: Homo sapiens

<400> SEQUENCE: 79

Leu Glu Cys Ser Ala Lys Thr Lys Glu Gly
1               5                   10

```
<210> SEQ ID NO 80
<211> LENGTH: 10
<212> TYPE: PRT
<213> ORGANISM: Homo sapiens

<400> SEQUENCE: 80

Glu Cys Ser Ala Lys Thr Lys Glu Gly Val
1               5                   10

<210> SEQ ID NO 81
<211> LENGTH: 10
<212> TYPE: PRT
<213> ORGANISM: Homo sapiens

<400> SEQUENCE: 81

Cys Ser Ala Lys Thr Lys Glu Gly Val Arg
1               5                   10

<210> SEQ ID NO 82
<211> LENGTH: 10
<212> TYPE: PRT
<213> ORGANISM: Homo sapiens

<400> SEQUENCE: 82

Ser Ala Lys Thr Lys Glu Gly Val Arg Glu
1               5                   10

<210> SEQ ID NO 83
<211> LENGTH: 9
<212> TYPE: PRT
<213> ORGANISM: Homo sapiens

<400> SEQUENCE: 83

Lys Thr Lys Glu Gly Val Arg Glu Val
1               5

<210> SEQ ID NO 84
<211> LENGTH: 9
<212> TYPE: PRT
<213> ORGANISM: Homo sapiens

<400> SEQUENCE: 84

Thr Lys Glu Gly Val Arg Glu Val Phe
1               5

<210> SEQ ID NO 85
<211> LENGTH: 10
<212> TYPE: PRT
<213> ORGANISM: Homo sapiens

<400> SEQUENCE: 85

Thr Lys Glu Gly Val Arg Glu Val Phe Glu
1               5                   10

<210> SEQ ID NO 86
<211> LENGTH: 10
<212> TYPE: PRT
<213> ORGANISM: Homo sapiens

<400> SEQUENCE: 86

Lys Glu Gly Val Arg Glu Val Phe Glu Met
1               5                   10

<210> SEQ ID NO 87
<211> LENGTH: 9
```

<212> TYPE: PRT
<213> ORGANISM: Homo sapiens

<400> SEQUENCE: 87

Gly Val Arg Glu Val Phe Glu Met Ala
1               5

<210> SEQ ID NO 88
<211> LENGTH: 10
<212> TYPE: PRT
<213> ORGANISM: Homo sapiens

<400> SEQUENCE: 88

Glu Val Phe Glu Met Ala Thr Arg Ala Gly
1               5                   10

<210> SEQ ID NO 89
<211> LENGTH: 10
<212> TYPE: PRT
<213> ORGANISM: Homo sapiens

<400> SEQUENCE: 89

Val Phe Glu Met Ala Thr Arg Ala Gly Leu
1               5                   10

<210> SEQ ID NO 90
<211> LENGTH: 10
<212> TYPE: PRT
<213> ORGANISM: Homo sapiens

<400> SEQUENCE: 90

Phe Glu Met Ala Thr Arg Ala Gly Leu Gln
1               5                   10

<210> SEQ ID NO 91
<211> LENGTH: 10
<212> TYPE: PRT
<213> ORGANISM: Homo sapiens

<400> SEQUENCE: 91

Glu Met Ala Thr Arg Ala Gly Leu Gln Val
1               5                   10

<210> SEQ ID NO 92
<211> LENGTH: 10
<212> TYPE: PRT
<213> ORGANISM: Homo sapiens

<400> SEQUENCE: 92

Met Ala Thr Arg Ala Gly Leu Gln Val Arg
1               5                   10

<210> SEQ ID NO 93
<211> LENGTH: 10
<212> TYPE: PRT
<213> ORGANISM: Homo sapiens

<400> SEQUENCE: 93

Ala Thr Arg Ala Gly Leu Gln Val Arg Lys
1               5                   10

<210> SEQ ID NO 94
<211> LENGTH: 10
<212> TYPE: PRT
<213> ORGANISM: Homo sapiens

<400> SEQUENCE: 94

Thr Arg Ala Gly Leu Gln Val Arg Lys Asn
1               5                   10

<210> SEQ ID NO 95
<211> LENGTH: 10
<212> TYPE: PRT
<213> ORGANISM: Homo sapiens

<400> SEQUENCE: 95

Arg Ala Gly Leu Gln Val Arg Lys Asn Lys
1               5                   10

<210> SEQ ID NO 96
<211> LENGTH: 10
<212> TYPE: PRT
<213> ORGANISM: Homo sapiens

<400> SEQUENCE: 96

Ala Gly Leu Gln Val Arg Lys Asn Lys Arg
1               5                   10

<210> SEQ ID NO 97
<211> LENGTH: 10
<212> TYPE: PRT
<213> ORGANISM: Homo sapiens

<400> SEQUENCE: 97

Gly Leu Gln Val Arg Lys Asn Lys Arg Arg
1               5                   10

<210> SEQ ID NO 98
<211> LENGTH: 10
<212> TYPE: PRT
<213> ORGANISM: Homo sapiens

<400> SEQUENCE: 98

Leu Gln Val Arg Lys Asn Lys Arg Arg Arg
1               5                   10

<210> SEQ ID NO 99
<211> LENGTH: 10
<212> TYPE: PRT
<213> ORGANISM: Homo sapiens

<400> SEQUENCE: 99

Gln Val Arg Lys Asn Lys Arg Arg Arg Gly
1               5                   10

<210> SEQ ID NO 100
<211> LENGTH: 10
<212> TYPE: PRT
<213> ORGANISM: Homo sapiens

<400> SEQUENCE: 100

Val Arg Lys Asn Lys Arg Arg Arg Gly Cys
1               5                   10

<210> SEQ ID NO 101
<211> LENGTH: 10
<212> TYPE: PRT
<213> ORGANISM: Homo sapiens

<400> SEQUENCE: 101

```
Arg Lys Asn Lys Arg Arg Arg Gly Cys Pro
1               5                   10

<210> SEQ ID NO 102
<211> LENGTH: 10
<212> TYPE: PRT
<213> ORGANISM: Homo sapiens

<400> SEQUENCE: 102

Lys Asn Lys Arg Arg Arg Gly Cys Pro Ile
1               5                   10

<210> SEQ ID NO 103
<211> LENGTH: 10
<212> TYPE: PRT
<213> ORGANISM: Homo sapiens

<400> SEQUENCE: 103

Asn Lys Arg Arg Arg Gly Cys Pro Ile Leu
1               5                   10

<210> SEQ ID NO 104
<211> LENGTH: 9
<212> TYPE: PRT
<213> ORGANISM: Homo sapiens

<400> SEQUENCE: 104

Val Pro Thr Val Phe Glu Asn Tyr Ile
1               5

<210> SEQ ID NO 105
<211> LENGTH: 9
<212> TYPE: PRT
<213> ORGANISM: Homo sapiens

<400> SEQUENCE: 105

Pro Thr Val Phe Glu Asn Tyr Ile Ala
1               5

<210> SEQ ID NO 106
<211> LENGTH: 9
<212> TYPE: PRT
<213> ORGANISM: Homo sapiens

<400> SEQUENCE: 106

Thr Val Phe Glu Asn Tyr Ile Ala Asp
1               5

<210> SEQ ID NO 107
<211> LENGTH: 9
<212> TYPE: PRT
<213> ORGANISM: Homo sapiens

<400> SEQUENCE: 107

Val Phe Glu Asn Tyr Ile Ala Asp Ile
1               5

<210> SEQ ID NO 108
<211> LENGTH: 9
<212> TYPE: PRT
<213> ORGANISM: Homo sapiens

<400> SEQUENCE: 108

Phe Glu Asn Tyr Ile Ala Asp Ile Glu
```

<210> SEQ ID NO 109
<211> LENGTH: 9
<212> TYPE: PRT
<213> ORGANISM: Homo sapiens

<400> SEQUENCE: 109

Glu Asn Tyr Ile Ala Asp Ile Glu Val
1               5

<210> SEQ ID NO 110
<211> LENGTH: 9
<212> TYPE: PRT
<213> ORGANISM: Homo sapiens

<400> SEQUENCE: 110

Asn Tyr Ile Ala Asp Ile Glu Val Asp
1               5

<210> SEQ ID NO 111
<211> LENGTH: 9
<212> TYPE: PRT
<213> ORGANISM: Homo sapiens

<400> SEQUENCE: 111

Tyr Ile Ala Asp Ile Glu Val Asp Gly
1               5

<210> SEQ ID NO 112
<211> LENGTH: 9
<212> TYPE: PRT
<213> ORGANISM: Homo sapiens

<400> SEQUENCE: 112

Ile Ala Asp Ile Glu Val Asp Gly Lys
1               5

<210> SEQ ID NO 113
<211> LENGTH: 9
<212> TYPE: PRT
<213> ORGANISM: Homo sapiens

<400> SEQUENCE: 113

Val Gly Asn Lys Lys Asp Leu Arg Gln
1               5

<210> SEQ ID NO 114
<211> LENGTH: 9
<212> TYPE: PRT
<213> ORGANISM: Homo sapiens

<400> SEQUENCE: 114

Gly Asn Lys Lys Asp Leu Arg Gln Asp
1               5

<210> SEQ ID NO 115
<211> LENGTH: 9
<212> TYPE: PRT
<213> ORGANISM: Homo sapiens

<400> SEQUENCE: 115

Asn Lys Lys Asp Leu Arg Gln Asp Glu
1               5

```
<210> SEQ ID NO 116
<211> LENGTH: 9
<212> TYPE: PRT
<213> ORGANISM: Homo sapiens

<400> SEQUENCE: 116

Lys Lys Asp Leu Arg Gln Asp Glu His
1               5

<210> SEQ ID NO 117
<211> LENGTH: 9
<212> TYPE: PRT
<213> ORGANISM: Homo sapiens

<400> SEQUENCE: 117

Lys Asp Leu Arg Gln Asp Glu His Thr
1               5

<210> SEQ ID NO 118
<211> LENGTH: 9
<212> TYPE: PRT
<213> ORGANISM: Homo sapiens

<400> SEQUENCE: 118

Lys Leu Arg Gln Asp Glu His Thr Arg
1               5

<210> SEQ ID NO 119
<211> LENGTH: 9
<212> TYPE: PRT
<213> ORGANISM: Homo sapiens

<400> SEQUENCE: 119

Leu Arg Gln Asp Glu His Thr Arg Arg
1               5

<210> SEQ ID NO 120
<211> LENGTH: 9
<212> TYPE: PRT
<213> ORGANISM: Homo sapiens

<400> SEQUENCE: 120

Arg Gln Asp Glu His Thr Arg Arg Glu
1               5

<210> SEQ ID NO 121
<211> LENGTH: 9
<212> TYPE: PRT
<213> ORGANISM: Homo sapiens

<400> SEQUENCE: 121

Gln Asp Glu His Thr Arg Arg Glu Leu
1               5

<210> SEQ ID NO 122
<211> LENGTH: 9
<212> TYPE: PRT
<213> ORGANISM: Homo sapiens

<400> SEQUENCE: 122

Ala Lys Met Lys Gln Glu Pro Val Arg
1               5

<210> SEQ ID NO 123
```

```
<211> LENGTH: 9
<212> TYPE: PRT
<213> ORGANISM: Homo sapiens

<400> SEQUENCE: 123

Lys Met Lys Gln Glu Pro Val Arg Ser
1               5

<210> SEQ ID NO 124
<211> LENGTH: 9
<212> TYPE: PRT
<213> ORGANISM: Homo sapiens

<400> SEQUENCE: 124

Met Lys Gln Glu Pro Val Arg Ser Glu
1               5

<210> SEQ ID NO 125
<211> LENGTH: 9
<212> TYPE: PRT
<213> ORGANISM: Homo sapiens

<400> SEQUENCE: 125

Lys Gln Glu Pro Val Arg Ser Glu Glu
1               5

<210> SEQ ID NO 126
<211> LENGTH: 9
<212> TYPE: PRT
<213> ORGANISM: Homo sapiens

<400> SEQUENCE: 126

Gln Glu Pro Val Arg Ser Glu Glu Gly
1               5

<210> SEQ ID NO 127
<211> LENGTH: 9
<212> TYPE: PRT
<213> ORGANISM: Homo sapiens

<400> SEQUENCE: 127

Glu Pro Val Arg Ser Glu Glu Gly Arg
1               5

<210> SEQ ID NO 128
<211> LENGTH: 9
<212> TYPE: PRT
<213> ORGANISM: Homo sapiens

<400> SEQUENCE: 128

Pro Val Arg Ser Glu Glu Gly Arg Asp
1               5

<210> SEQ ID NO 129
<211> LENGTH: 9
<212> TYPE: PRT
<213> ORGANISM: Homo sapiens

<400> SEQUENCE: 129

Val Arg Ser Glu Glu Gly Arg Asp Met
1               5

<210> SEQ ID NO 130
<211> LENGTH: 9
<212> TYPE: PRT
```

<213> ORGANISM: Homo sapiens

<400> SEQUENCE: 130

Arg Ser Glu Glu Gly Arg Asp Met Ala
1               5

<210> SEQ ID NO 131
<211> LENGTH: 9
<212> TYPE: PRT
<213> ORGANISM: Homo sapiens

<400> SEQUENCE: 131

Ser Glu Glu Gly Arg Asp Met Ala Asn
1               5

<210> SEQ ID NO 132
<211> LENGTH: 9
<212> TYPE: PRT
<213> ORGANISM: Homo sapiens

<400> SEQUENCE: 132

Gly Arg Asp Met Ala Asn Arg Ile Ser
1               5

<210> SEQ ID NO 133
<211> LENGTH: 9
<212> TYPE: PRT
<213> ORGANISM: Homo sapiens

<400> SEQUENCE: 133

Arg Asp Met Ala Asn Arg Ile Ser Ala
1               5

<210> SEQ ID NO 134
<211> LENGTH: 9
<212> TYPE: PRT
<213> ORGANISM: Homo sapiens

<400> SEQUENCE: 134

Asp Met Ala Asn Arg Ile Ser Ala Phe
1               5

<210> SEQ ID NO 135
<211> LENGTH: 9
<212> TYPE: PRT
<213> ORGANISM: Homo sapiens

<400> SEQUENCE: 135

Met Ala Asn Arg Ile Ser Ala Phe Gly
1               5

<210> SEQ ID NO 136
<211> LENGTH: 9
<212> TYPE: PRT
<213> ORGANISM: Homo sapiens

<400> SEQUENCE: 136

Ala Asn Arg Ile Ser Ala Phe Gly Tyr
1               5

<210> SEQ ID NO 137
<211> LENGTH: 9
<212> TYPE: PRT
<213> ORGANISM: Homo sapiens

```
<400> SEQUENCE: 137

Asn Arg Ile Ser Ala Phe Gly Tyr Leu
1               5

<210> SEQ ID NO 138
<211> LENGTH: 9
<212> TYPE: PRT
<213> ORGANISM: Homo sapiens

<400> SEQUENCE: 138

Arg Ile Ser Ala Phe Gly Tyr Leu Glu
1               5

<210> SEQ ID NO 139
<211> LENGTH: 9
<212> TYPE: PRT
<213> ORGANISM: Homo sapiens

<400> SEQUENCE: 139

Ile Ser Ala Phe Gly Tyr Leu Glu Cys
1               5

<210> SEQ ID NO 140
<211> LENGTH: 9
<212> TYPE: PRT
<213> ORGANISM: Homo sapiens

<400> SEQUENCE: 140

Ser Ala Phe Gly Tyr Leu Glu Cys Ser
1               5

<210> SEQ ID NO 141
<211> LENGTH: 9
<212> TYPE: PRT
<213> ORGANISM: Homo sapiens

<400> SEQUENCE: 141

Ala Phe Gly Tyr Leu Glu Cys Ser Ala
1               5

<210> SEQ ID NO 142
<211> LENGTH: 9
<212> TYPE: PRT
<213> ORGANISM: Homo sapiens

<400> SEQUENCE: 142

Phe Gly Tyr Leu Glu Cys Ser Ala Lys
1               5

<210> SEQ ID NO 143
<211> LENGTH: 9
<212> TYPE: PRT
<213> ORGANISM: Homo sapiens

<400> SEQUENCE: 143

Gly Tyr Leu Glu Cys Ser Ala Lys Thr
1               5

<210> SEQ ID NO 144
<211> LENGTH: 10
<212> TYPE: PRT
<213> ORGANISM: Homo sapiens

<400> SEQUENCE: 144
```

Gly Tyr Leu Glu Cys Ser Ala Lys Thr Lys
1               5                   10

<210> SEQ ID NO 145
<211> LENGTH: 10
<212> TYPE: PRT
<213> ORGANISM: Homo sapiens

<400> SEQUENCE: 145

Tyr Leu Glu Cys Ser Ala Lys Thr Lys Glu
1               5                   10

<210> SEQ ID NO 146
<211> LENGTH: 10
<212> TYPE: PRT
<213> ORGANISM: Homo sapiens

<400> SEQUENCE: 146

Leu Glu Cys Ser Ala Lys Thr Lys Glu Gly
1               5                   10

<210> SEQ ID NO 147
<211> LENGTH: 10
<212> TYPE: PRT
<213> ORGANISM: Homo sapiens

<400> SEQUENCE: 147

Glu Cys Ser Ala Lys Thr Lys Glu Gly Val
1               5                   10

<210> SEQ ID NO 148
<211> LENGTH: 10
<212> TYPE: PRT
<213> ORGANISM: Homo sapiens

<400> SEQUENCE: 148

Cys Ser Ala Lys Thr Lys Glu Gly Val Arg
1               5                   10

<210> SEQ ID NO 149
<211> LENGTH: 10
<212> TYPE: PRT
<213> ORGANISM: Homo sapiens

<400> SEQUENCE: 149

Ser Ala Lys Thr Lys Glu Gly Val Arg Glu
1               5                   10

<210> SEQ ID NO 150
<211> LENGTH: 9
<212> TYPE: PRT
<213> ORGANISM: Homo sapiens

<400> SEQUENCE: 150

Lys Thr Lys Glu Gly Val Arg Glu Val
1               5

<210> SEQ ID NO 151
<211> LENGTH: 10
<212> TYPE: PRT
<213> ORGANISM: Homo sapiens

<400> SEQUENCE: 151

Lys Thr Lys Glu Gly Val Arg Glu Val Phe
1               5                   10

<210> SEQ ID NO 152
<211> LENGTH: 9
<212> TYPE: PRT
<213> ORGANISM: Homo sapiens

<400> SEQUENCE: 152

Lys Glu Gly Val Arg Glu Val Phe Glu
1               5

<210> SEQ ID NO 153
<211> LENGTH: 9
<212> TYPE: PRT
<213> ORGANISM: Homo sapiens

<400> SEQUENCE: 153

Glu Gly Val Arg Glu Val Phe Glu Met
1               5

<210> SEQ ID NO 154
<211> LENGTH: 9
<212> TYPE: PRT
<213> ORGANISM: Homo sapiens

<400> SEQUENCE: 154

Val Phe Glu Met Ala Thr Arg Ala Gly
1               5

<210> SEQ ID NO 155
<211> LENGTH: 9
<212> TYPE: PRT
<213> ORGANISM: Homo sapiens

<400> SEQUENCE: 155

Phe Glu Met Ala Thr Arg Ala Gly Leu
1               5

<210> SEQ ID NO 156
<211> LENGTH: 10
<212> TYPE: PRT
<213> ORGANISM: Homo sapiens

<400> SEQUENCE: 156

Phe Glu Met Ala Thr Arg Ala Gly Leu Gln
1               5                   10

<210> SEQ ID NO 157
<211> LENGTH: 9
<212> TYPE: PRT
<213> ORGANISM: Homo sapiens

<400> SEQUENCE: 157

Met Ala Thr Arg Ala Gly Leu Gln Val
1               5

<210> SEQ ID NO 158
<211> LENGTH: 9
<212> TYPE: PRT
<213> ORGANISM: Homo sapiens

<400> SEQUENCE: 158

Ala Thr Arg Ala Gly Leu Gln Val Arg
1               5

<210> SEQ ID NO 159
<211> LENGTH: 9
<212> TYPE: PRT
<213> ORGANISM: Homo sapiens

<400> SEQUENCE: 159

Thr Arg Ala Gly Leu Gln Val Arg Lys
1               5

<210> SEQ ID NO 160
<211> LENGTH: 9
<212> TYPE: PRT
<213> ORGANISM: Homo sapiens

<400> SEQUENCE: 160

Arg Ala Gly Leu Gln Val Arg Lys Asn
1               5

<210> SEQ ID NO 161
<211> LENGTH: 9
<212> TYPE: PRT
<213> ORGANISM: Homo sapiens

<400> SEQUENCE: 161

Ala Gly Leu Gln Val Arg Lys Asn Lys
1               5

<210> SEQ ID NO 162
<211> LENGTH: 9
<212> TYPE: PRT
<213> ORGANISM: Homo sapiens

<400> SEQUENCE: 162

Gly Leu Gln Val Arg Lys Asn Lys Arg
1               5

<210> SEQ ID NO 163
<211> LENGTH: 9
<212> TYPE: PRT
<213> ORGANISM: Homo sapiens

<400> SEQUENCE: 163

Leu Gln Val Arg Lys Asn Lys Arg Arg
1               5

<210> SEQ ID NO 164
<211> LENGTH: 9
<212> TYPE: PRT
<213> ORGANISM: Homo sapiens

<400> SEQUENCE: 164

Gln Val Arg Lys Asn Lys Arg Arg Arg
1               5

<210> SEQ ID NO 165
<211> LENGTH: 9
<212> TYPE: PRT
<213> ORGANISM: Homo sapiens

<400> SEQUENCE: 165

Val Arg Lys Asn Lys Arg Arg Arg Gly
1               5

<210> SEQ ID NO 166
<211> LENGTH: 9

```
<212> TYPE: PRT
<213> ORGANISM: Homo sapiens

<400> SEQUENCE: 166

Arg Lys Asn Lys Arg Arg Arg Gly Cys
 1               5

<210> SEQ ID NO 167
<211> LENGTH: 9
<212> TYPE: PRT
<213> ORGANISM: Homo sapiens

<400> SEQUENCE: 167

Lys Asn Lys Arg Arg Arg Gly Cys Pro
 1               5

<210> SEQ ID NO 168
<211> LENGTH: 9
<212> TYPE: PRT
<213> ORGANISM: Homo sapiens

<400> SEQUENCE: 168

Asn Lys Arg Arg Arg Gly Cys Pro Ile
 1               5

<210> SEQ ID NO 169
<211> LENGTH: 9
<212> TYPE: PRT
<213> ORGANISM: Homo sapiens

<400> SEQUENCE: 169

Lys Arg Arg Arg Gly Cys Pro Ile Leu
 1               5

<210> SEQ ID NO 170
<211> LENGTH: 10
<212> TYPE: PRT
<213> ORGANISM: Homo sapiens

<400> SEQUENCE: 170

Asp Lys Leu Arg Gln Asp Glu His Thr Arg
 1               5                  10

<210> SEQ ID NO 171
<211> LENGTH: 10
<212> TYPE: PRT
<213> ORGANISM: Homo sapiens

<400> SEQUENCE: 171

Arg Gln Asp Glu His Thr Arg Arg Glu Leu
 1               5                  10

<210> SEQ ID NO 172
<211> LENGTH: 10
<212> TYPE: PRT
<213> ORGANISM: Homo sapiens

<400> SEQUENCE: 172

Gln Asp Glu His Thr Arg Arg Glu Leu Ala
 1               5                  10

<210> SEQ ID NO 173
<211> LENGTH: 10
<212> TYPE: PRT
<213> ORGANISM: Homo sapiens
```

```
<400> SEQUENCE: 173

Ala Asn Arg Ile Ser Ala Phe Gly Tyr Leu
1               5                   10

<210> SEQ ID NO 174
<211> LENGTH: 10
<212> TYPE: PRT
<213> ORGANISM: Homo sapiens

<400> SEQUENCE: 174

Arg Ile Ser Ala Phe Gly Tyr Leu Glu Cys
1               5                   10

<210> SEQ ID NO 175
<211> LENGTH: 10
<212> TYPE: PRT
<213> ORGANISM: Homo sapiens

<400> SEQUENCE: 175

Ser Ala Phe Gly Tyr Leu Glu Cys Ser Ala
1               5                   10

<210> SEQ ID NO 176
<211> LENGTH: 10
<212> TYPE: PRT
<213> ORGANISM: Homo sapiens

<400> SEQUENCE: 176

Ala Lys Thr Lys Glu Gly Val Arg Glu Val
1               5                   10

<210> SEQ ID NO 177
<211> LENGTH: 10
<212> TYPE: PRT
<213> ORGANISM: Homo sapiens

<400> SEQUENCE: 177

Glu Gly Val Arg Glu Val Phe Glu Met Ala
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Variant of a sequence from humans, Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 178

Arg Xaa Gly Leu Gln Val Arg Lys Asn Lys
1               5                   10
```

RHOC-BASED IMMUNOTHERAPY

This application is a National Stage Application of PCT/DK2008/050324, filed 18 Dec. 2008, which claims benefit of Serial No. PA 2007 01844, filed 19 Dec. 2007 in Denmark and which applications are incorporated herein by reference. To the extent appropriate, a claim of priority is made to each of the above disclosed applications.

All patent and non-patent references cited in the application, or in the present application, are also hereby incorporated by reference in their entirety.

FIELD OF INVENTION

The present invention relates generally to the field of prophylaxis and therapy of metastatic cancer. In particular there is provided a protein; Ras Homology gene family, member C (RhoC) or peptide fragments thereof that are capable of eliciting anti-cancer immune responses. Specifically, the invention relates to use of RhoC or peptides derived thereof or RhoC specific T-cells for treatment of metastatic cancer. Hence, the invention in one aspect relates to RhoC specific T-cells adoptively transferred or induced in vivo by vaccination as a treatment of cancer.

Also the use of RhoC and immunogenic peptide fragments hereof in cancer treatment, diagnosis and prognosis is provided.

BACKGROUND OF INVENTION

The development of metastasis in cancer poses a major obstacle in the successful treatment of cancer. Most cancer deaths are caused by the development of metastases.

The search for proteins responsible for metastasis has implicated Ras homology gene family GTPase RhoC. Overexpression of RhoC has been suggested to play a role in the development of metastasis. Although a precise understanding of how RhoC exerts its metastatic effects remains elusive, it has been found to be overexpressed in many cancers including ovarian cancer, lung cancer and melanomas.

The process by which the mammalian immune system recognises and reacts to foreign or alien materials is a complex one. An important facet of the system is the T-cell response. This response requires that T cells recognise and interact with complexes of cell surface molecules referred to as human leukocyte antigens (HLA) constituting the human major histocompatibility complex (MHC), and peptides. The peptides are derived from larger molecules, which are processed by the antigen presenting cells, which in turn present the HLA/MHC molecule. The interaction of T cells and complexes of HLA/peptide is restricted, requiring a T cell that is specific for a particular combination of an HLA molecule and a peptide. If a specific T cell is not present, there is no T-cell response even if its partner complex is present. Similarly, there is no response if the specific complex is absent, but the T cell is present.

The mechanism by which T cells recognise cellular abnormalities has also been implicated in cancer. E.g. in WO92/20356, a family of genes is disclosed which are processed into peptides which, in turn, are expressed on cells surfaces, and can lead to lysis of the tumour cells by specific cytotoxic T ymphocytes (CTLs, CD8 cells). These genes are referred to as the MAGE family and are said to code for "tumour rejection antigen precursors" or "TRAP" molecules, and the peptides derived there from are referred to as "tumour rejection antigens" or "TRAs".

In WO 94/05304, nonapeptides are disclosed which bind to the HLA-A1 molecule. This reference discloses that, given the known specificity of particular peptides for particular HLA molecules, one should expect a particular peptide to bind one HLA molecule, but not others. This is significant, as different individuals possess different HLA phenotypes. As a result, while identification of a particular peptide as being a partner for a specific HLA molecule has diagnostic and therapeutic ramifications, these are only relevant for individuals with that particular HLA phenotype.

Thus, it is well established that peptide epitopes derived from tumour associated antigens (TAAs) can be recognised as antigens by CTLs in the context of MHC molecules. However, although it is generally accepted that most if not all, tumours are antigenic, only a few are indeed immunogenic in the sense that tumour progression is readily controlled by the immune system.

To overcome this limitation, several immunotherapeutic studies have been initiated, e.g. vaccinations with TAA-derived peptides. For melanoma, the tumour for which the largest number of CTL-defined TAAs has been characterised, powerful CTL responses against antigens have been induced by vaccination and some patients experienced a complete remission of their disease. However, most of the peptide epitopes used in these vaccination trials are melanocyte specific, and these peptides cannot be applied for tumours of non-melanocyte origin. Furthermore, expression of these TAAs is heterogeneous among tumours from different patients and can even vary among metastases obtained from one patient. However, during the last couple of years a number of tumour specific peptide antigens, which are expressed in a number of different cancers, have been identified, i.e. HER-2, Muc-1 and telomerase.

During the past decade numerous clinical trials have shown the feasibility of peptide specific vaccination to induce anti-tumor T-cell responses in cancer patients. The clinical course of the patients, however, was in most cases not improved. This discrepancy has in numerous cases been explained by immune escape mechanisms of the tumour cells.

Like the other Rho GTPases, RhoC affect several aspects of growth control, and cytoskeletal organization in response to extracellular factors. More recent data suggests a more differential role in that RhoC has been shown to play an important role in metastasising cancer cells. Thus, several lines of evidence demonstrate a high expression of RhoC in cancer cells, and that the metastatic potential of cancer cells depends on expression of RhoC. Selective increased expression of RhoC has been described in metastatic cancers.

SUMMARY OF THE INVENTION

The present invention is based on the surprising finding that MHC Class I and Class II restricted peptides can be derived from RhoC, said peptides being capable of binding to MHC Class I and Class II molecules. Surprisingly, the inventors found that these self-antigens were capable of eliciting a spontaneous T-cell response in patients suffering from cancer diseases in particular metastatic cancer diseases. These findings open the way for novel therapeutic and diagnostic approaches which may be generally applicable in the control of metastatic cancer diseases.

There has been difficulty in finding appropriate protein targets specifically for designing a vaccine against metastasis. The present invention discloses novel RhoC peptides, some of which are recognized by cytotoxic (CD8) and some of which are recognized by helper (CD4) T cells. These epitopes are restricted by Class II and Class I MHC proteins respectively.

A focus of the present invention is thus on eliciting tumor-specific T cell immunity, i.e., vaccinating with class I and class II-MHC restricted epitopes despite the fact that tumors generally do not express class II MHC. This is based on the finding that the induction and efficacy of the vaccine-induced anti-tumor response to RhoC may require the cooperation of tumor-specific CD4 positive $T_h$ cells.

Thus, in one aspect an important factor driving the development of the vaccines may be the desire to target multiple tumor antigens e.g. by designing vaccines comprising or encoding a collection of carefully selected CTL and $T_h$ cell epitopes. Multi-epitope vaccines may constitute an efficient way to raise immunity against epitopes derived from several different antigens without the need for introducing (genes encoding) potentially hazardous proteins such as oncoproteins. Such vaccines also permit selective induction of immunity against subdominant and cryptic T cell epitopes, which can be especially important in the case of tumor-associated autoantigens for which tolerance may exist for the epitopes that are prominently presented in normal tissues. Furthermore, antigen-presenting cells may fail to present certain epitopes that are expressed on tumor cells because of functional differences between the immunoproteasomes of antigen-presenting cells and the 'constitutive' proteasomes present in most tumor cells.

In the case of peptide-based vaccines, epitopes can be administered in an 'MHC-ready' form, which enables presentation through exogenous loading independently of antigen uptake and processing by host antigen-presenting cells. The peptides of the present invention comprise both peptides in a short 'MHC-ready' form and in a longer form requiring processing by the proteasome thus providing a more complex vaccine composition that can target multiple tumor antigens. The more different HLA groups are targeted by a vaccine, the higher likelihood of the vaccine functioning in diverse populations.

The present invention discloses that RhoC is as a suitable target for immunotherapy against metastatic cancer. The expression of RhoC has been proposed to promote metastasis, which potentially makes RhoC an attractive target for vaccination because immune escape by down-regulation or loss of expression of this protein could impair metastasis. The inventors searched for and surprisingly detected spontaneous T-cell reactivity in peripheral blood lymphocytes (PBL) against RhoC derived peptides in melanoma patients using an ELISPOT assay.

Accordingly, the present invention pertains in a first aspect to

A vaccine composition comprising
a) RhoC of SEQ ID NO 1 or a functional homologue thereof having at least 70% identity to SEQ ID NO 1 or an immunogenically active peptide fragment comprising a consecutive sequence of said RhoC or said functional homologue thereof or a nucleic acid encoding said RhoC or said peptide fragment; and
b) an adjuvant
for use as a medicament.

Other aspects of the invention relates to RhoC or a peptide fragment hereof for use as a medicament in the prevention or treatment of metastatic cancer.

In particular the invention relates to an isolated immunogenically active peptide fragment consisting of 18 to 25 consecutive amino acids from RhoC of SEQ ID NO 1 or a functional homologue of said peptide fragment, wherein at the most three amino acids have been substituted, wherein the peptide fragment contains at least one of amino acid residues I43, Q123, R140, S141, S152, L157, E165, G178, V181, K183, N184, R186, R187, R188, P191 or I192 of RhoC of SEQ ID no 1.

Also, the invention relates to isolated immunogenically active peptide fragment consisting of 8 to 10 consecutive amino acids from RhoC of SEQ ID no 1 or a functional homologue of said peptide fragment, wherein at the most three amino acids have been substituted, wherein the peptide fragment contains at least one of amino acid residues I43, Q123, R140, S141, S152, L157, E165, G178, V181, K183, N184, R186, R187, R188, P191 or I192 of RhoC of SEQ ID no 1.

Further, the invention also relates to isolated immunogenically active peptide fragment consisting of 26 to 75 consecutive amino acids from RhoC of SEQ ID no 1 or a functional homologue thereof wherein at the most two amino acid have been substituted, wherein the peptide fragment contains at least one of amino acid residues I43, Q123, R140, S141, S152, L157, E165, G178, V181, K183, N184, R186, R187, R188, P191 or I192 of RhoC of SEQ ID no 1

Thus, the present invention pertains in a second aspect to immunogenically active peptide fragments of RhoC for use as a medicament in the prevention or treatment of metastatic cancer. In particular, the invention pertains to isolated immunogenically active peptide fragments derived from RhoC for use as a medicament in the prevention or treatment of metastatic cancer.

In a further aspect, the invention provides a pharmaceutical composition comprising the above protein and/or peptide fragments of the invention.

It is also an aspect of the invention to provide a vaccine composition comprising RhoC or an immunogenically active peptide fragment hereof or a nucleic acid encoding said protein or said peptide fragment for use as a medicament in the prevention or treatment of metastatic cancer.

In still further aspects the invention relates to a diagnostic kit for ex vivo or in situ diagnosis of the presence in a cancer patient of T cells in PBLs or in tumor tissue that are reactive with RhoC, the kit comprising the peptide fragment of the invention as defined above; a complex of a peptide fragment of the invention and a Class I or class II HLA molecule or a fragment of such molecule.

It is also an objective of the invention to provide a method of detecting in a metastatic cancer patient the presence of RhoC reactive T cells, the method comprising contacting a tumour tissue or a blood sample with a complex of the invention as defined above and detecting binding of the complex to the tissue or the blood cells.

Additionally, there is provided a molecule that is capable of binding specifically to a peptide fragment of the invention and a molecule that is capable of blocking such binding.

In another aspect the invention pertains to a method of treating a metastatic cancer disease, the method comprising administering to a patient suffering from the disease an effective amount of the pharmaceutical composition of the invention, the molecule of the invention that is capable of binding specifically to a peptide fragment of the invention and/or a molecule of the invention that is capable of blocking such binding.

In yet another aspect the invention provides the use of the protein or peptide fragment as defined herein in the manufacturing of a medicament for the treatment of a cancer disease.

Additionally there is provided RhoC of SEQ ID NO 1 or a functional homologue thereof having at least 70% identity to SEQ ID NO 1 or an immunogenically active peptide fragment comprising a consecutive sequence of said RhoC or said functional homologue thereof or a nucleic acid encoding said RhoC or said peptide fragment for use in the treatment or prevention of metastatic cancer.

Further is provided the peptide fragment as defined herein or the vaccine composition as defined herein for use in the treatment or prevention of metastatic cancer.

Another aspect of the invention relates to s method of monitoring immunisation, said method comprising the steps of
  i) providing a blood sample from an individual
  ii) providing RhoC of SEQ ID NO 1 or a functional homologue thereof having at least 70% identity to SEQ ID NO 1 or an immunogenically active peptide fragment comprising a consecutive sequence of said RhoC or said functional homologue thereof or a nucleic acid encoding said RhoC or said peptide fragment.
  iii) determining whether said blood sample comprises antibodies or T-cells comprising T-cell receptors specifically binding the protein or peptide
  iv) thereby determining whether an immune response to said protein or peptide has been raised in said individual.

Another aspect of the invention relates to isolated T cells that are capable of specifically interacting with RhoC or peptide fragments hereof and a method of producing said T cells.

Yet another aspect of the invention provides a pharmaceutical composition comprising the isolated RhoC specific T-cell clone and a method of treating and/or preventing metastatic cancer comprising administering to an individual in need thereof a composition comprising the isolated RhoC specific T-cells.

DETAILED DESCRIPTION OF THE INVENTION

It is a major objective of the present invention to provide RhoC or an immunologically active peptide fragment hereof for use as a medicament in the prevention or treatment of a cancer.

The Rho GTPases

The three human Rho family members RhoA, B and C are highly homologous, with RhoA and RhoC being the most homologous. RhoA and RhoC are both 193 amino acids long, whereas RhoC consists of 191 amino acids. Despite RhoA and RhoC being highly homologoues there is extensive heterogeneity in the C-terminal of the sequence between RhoA and RhoC. FIG. 1 shows an alignment of RhoA; RhoB and RhoC, wherein identical residues ("*") and residues with conservative (":") and semi-conservative (".") substitutions are marked.

The N-terminal half of Rho GTPases contains the majority of the amino acids involved in GTP binding and hydrolysis, together with the Switch 1 and 2 regions that change conformation between the GTP-bound and GDP-bound states (Bishop, A. L., Hall, A., Biochem. J. 2000, 348 (Pt. 2):241).

The C-terminus of Rho family GTPases is essential for correct localization of the proteins. It is modified post-translationally by prenylation of a conserved C-terminal cysteine, followed by methylation and proteolytic removal of the last three amino acids (Shao, F., Dixon, J. E., Adv. Exp. Med. Biol. 2003, 529:79). The prenyl group anchors the GTPases into membranes and this modification is essential for the cell growth, transformation, and cytoskeleton organization functions of the Rho proteins (Allal, C., et al., J. Biol. Chem. 2000, 275:31001). Prenylation of Rho proteins appears to be important for their stability, inhibitors of enzymes that synthesize prenyl groups induce a decrease in Rho protein levels and their function (Stamatakis, K., et al., J. Biol. Chem 2002, 277:49389).

RhoA

RhoA is over-expressed in several human cancers, and it appears that RhoA overexpression correlates with poor prognosis. Several reports also demonstrate the implication of RhoA in angiogenesis, which aids growth of solid tumours and metastasis (Abecassis et al., 2003). While activation of cytoskeletal assembly most often results in the growth or extension of a cell, in neurons, Rho family proteins have been shown to induce neurite retraction and cause cell rounding.

In some embodiments of the invention the peptide fragments of the invention are common to both RhoA of SEQ ID NO 2 and RhoC of SEQ ID NO 1. In preferred embodiments however, the peptide fragments of the invention are specific to human RhoC of SEQ ID NO 1 only.

RhoC

Recent data have shown RhoC to play an important role in metastasising cancer cells. Studies have indicated that Rho protein-dependant cell signalling might be important for malignant transformation. RhoC has been shown to be involved in cancer invasion in melanoma, inflammatory breast cancer (Clark et al., 2000; Kleer et al., 2002), and ovarian cancer (Horiuchi et al., 2003).

Generally it has been difficult to design cancer vaccines directed to self-antigens as the immune system rarely elicits a response against 'self' proteins. Surprisingly, the RhoC peptides of the present invention were capable of eliciting a spontaneous T-cell response in patients suffering from cancer diseases in particular metastatic cancer diseases.

The present invention discloses that RhoC is as a suitable target for immunotherapy against metastatic cancer. The expression of RhoC has been proposed to promote metastasis, which potentially makes RhoC an attractive target for vaccination because immune escape by down-regulation or loss of expression of this protein could impair metastasis. The inventors surprisingly detected spontaneous T-cell reactivity in peripheral blood lymphocytes (PBL) against RhoC derived peptides in melanoma patients using an ELISPOT assay, which demonstrates that RhoC peptide fragments indeed may be useful T-cell epitopes.

In a preferred embodiment of the invention RhoC is human RhoC, more preferably human RhoC of SEQ ID NO 1.

In preferred embodiments of the invention, the RhoC peptides are selected from amino acid residues, which differ from the sequence of RhoB. In more preferred embodiments the RhoC peptides are peptides comprising amino acid residues, which differ from the sequence of both RhoA and RhoB. Accordingly in very preferred embodiments the peptide fragments of the invention contains at least one of amino acid residues I43, Q123, R140, S141, S152, L157, E165, G178, V181, K183, N184, R186, R187, R188, P191 or I192 of RhoC of SEQ ID no 1.

In less preferred embodiments the RhoC peptides are peptides comprising amino acid residues, which differ from the sequence of RhoB, but are the same as the sequence of RhoA. Accordingly in less preferred embodiments the peptide fragments of the invention contains at least one of amino acid residues L81, M82, C83, F84, S85, I86, D87, S88, P89, D90, S91, L92, E93, N94, I95, K98, W99, T100, P101, E102, V103, K104, H105, F106, C107, P108, N109, P111, I112, I113, V115, G116, N117, K118, K119, T127, R129, E142, E143, D146, N149, F154, D155, G166, V167, R168, E169, V170, F171, E172, M173, A174, T175, R176, A177, L179, Q180, R182, K185, G189, C190.

As described herein above, RhoC mainly differs from RhoA and RhoB in the C-terminal part of the sequence. As only RhoC appears to have an influence on the metastatic potential of a tumour, preferred embodiments pertains to peptides of RhoC that are derived from the 120 most C-terminal residues of RhoC, such as the 100 most C-terminal residues of RhoC, for example the 75 most C-terminal residues of RhoC, such as 52 most C-terminal residues of RhoC, for example the 40 most C-terminal residues of RhoC, such as the 30 most C-terminal residues of RhoC, for example the 25 most C-terminal residues of RhoC, such as the 24 most C-terminal residues of RhoC, such as the 23 most C-terminal residues of RhoC, for example the 22 most C-terminal residues of RhoC, such as the 21 most C-terminal residues of RhoC, such as the 20 most C-terminal residues of RhoC, for example the 19 most C-terminal residues of RhoC, such as the 18 most C-terminal residues of RhoC, such as the 17 most C-terminal residues of RhoC, such as the 16 most C-terminal residues of RhoC, for example the 15 most C-terminal residues of RhoC, such as the 14 most C-terminal residues of RhoC of SEQ ID NO 1. Most preferred is a peptide consisting of the 20 most C-terminal residues of RhoC of SEQ ID NO 1.

Accordingly in very preferred embodiments the peptide fragments of the invention contains at least one of the 20 most C-terminal RhoC specific amino acid residues G178, V181, K183, N184, R186, R187, R188, P191 or I192 of RhoC of SEQ ID no 1.

In a specific embodiment of the invention the peptide fragment of the invention consist of the 20 most C-terminal amino acid residues of RhoC of SEQ ID NO 1. Accordingly in this particular embodiment the peptide is ATRAGLQVRKNKRRRGCPIL (SEQ ID NO 4).

In other specific embodiments of the invention the peptide fragment of the invention comprises the sequence RXGLQVRKNK SEQ ID NO: 178, wherein X is selected from the group consisting of alanine and leucine and wherein said peptide fragment is at the most 60 amino acids in length.

Functional Homologues

The wild-type human RhoC i.e. the naturally occurring non-mutated version of the protein is identified as SEQ ID NO: 1. The present invention covers immunologically active peptide fragments of RhoC. The present invention also covers vaccine compositions comprising RhoC, peptide fragments of RhoC, wherein at the most two amino acids have been substituted or functional homologues of RhoC comprising a sequence identity of at least 70% to SEQ ID NO: 1.

A functional homologue can be defined as RhoC that differs in sequence from the wild-type RhoC, such as wild-type human RhoC, but is still capable of inducing an immune response to cancers expressing wild-type RhoC. A functional homologue may be a mutated version or an alternative splice variant of the wild-type RhoC. In another aspect functional homologues of RhoC are defined as described herein below. A functional homologue may be, but is not limited to, a recombinant version of RhoC with one or more mutations and/or one or more sequence deletions and/or additions introduced ex vivo.

A functional homologue of RhoC may be any protein that exhibits at least some sequence identity with SEQ ID NO: 7 and has the capability to induce an immune response to cancers expressing wild-type RhoC.

Accordingly, in one embodiment of the invention it is preferred that functional homologues of RhoC comprise a sequence with high sequence identity to SEQ ID NO: 1, wherein none of the RhoC specific residues Q123, R140, S141, S152, L157, E165, G178, V181, K183, N184, R186, R187, R188, P191 or P192, which are marked in "bold characters" in FIG. 1 are substituted.

Further, in less preferred embodiments of the invention it is preferred that functional homologues of RhoC comprise a sequence with high sequence identity to SEQ ID NO: 1, wherein none of the amino acid residues that are RhoA and RhoC specific L81, M82, C83, F84, S85, I86, D87, S88, P89, D90, S91, L92, E93, N94, I95, K98, W99, T100, P101, E102, V103, K104, H105, F106, C107, P108, N109, P111, I112, I113, V115, G116, N117, K118, K119, T127, R129, E142, E143, D146, N149, F154, D155, G166, V167, R168, E169, V170, F171, E172, M173, A174, T175, R176, A177, L179, Q180, R182, K185, G189, C190, which are marked with a "*" in FIG. 1 are substituted.

Thus in one embodiment it is preferred that functional homologues of RhoC have a sequence with high sequence identity to SEQ ID NO: 1, wherein the RhoC specific amino acid residues Q123, R140, S141, S152, L157, E165, G178, V181, K183, N184, R186, R187, R188, P191 or P192 are either not substituted or substituted only by conservative substitution, more preferably substituted only an amino acid with a high level of similarity as defined herein below. Even more preferably these residues are not substituted at all.

Further, in less preferred embodiments of the invention it is preferred that functional homologues of RhoC comprise a sequence with high sequence identity to SEQ ID NO: 1, wherein none of the RhoA and RhoC specific amino acid residues L81, M82, C83, F84, S85, I86, D87, S88, P89, D90, S91, L92, E93, N94, I95, K98, W99, T100, P101, E102, V103, K104, H105, F106, C107, P108, N109, P111, I112, I113, V115, G116, N117, K118, K119, T127, R129, E142, E143, D146, N149, F154, D155, G166, V167, R168, E169, V170, F171, E172, M173, A174, T175, R176, A177, L179, Q180, R182, K185, G189, C190, which are marked with a "*" in FIG. 1 are either not substituted or substituted only by conservative substitution, more preferably substituted only an amino acid with a high level of similarity as defined herein below. Even more preferably these residues are not substituted at all.

A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Within the meaning of the term "conservative amino acid substitution" as applied herein, one amino acid may be substituted for another within the groups of amino acids indicated herein below:
Lower Levels of Similarity:
Polarity:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
Hydrophilic or Hydrophobic:
iii) Hydrophobic amino acids (Ala, Cys, Gly, Ile, Leu, Met, Phe, Pro, Trp, Tyr, Val)
iv) Hydrophilic amino acids (Arg, Ser, Thr, Asn, Asp, Gln, Glu, His, Lys)
Charges:
v) Neutral amino acids (Ala, Asn, Cys, Gln, Gly, Ile, Leu, Met, Phe, Pro, Ser, Thr, Trp, Tyr, Val)
vi) Basic amino acids (Arg, His, Lys)
vii) Acidic amino acids ((asp, Glu)
High Level of Similarity:
viii) Acidic amino acids and their amides (Gln, Asn, Glu, Asp)
ix) Amino acids having aliphatic side chains (Gly, Ala Val, Leu, Ile)
x) Amino acids having aromatic side chains (Phe, Tyr, Trp)
xi) Amino acids having basic side chains (Lys, Arg, His)
xii) Amino acids having hydroxy side chains (Ser, Thr)
xiii) Amino acids having sulphor-containing side chains (Cys, Met), Preferred conservative amino acids substitution groups are: valine-leucine-isoleucine, phenylalanine-tyrosine, lysine-arginine, alanine-valine, and asparagine-glutamine.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

Aside from the twenty standard amino acids and two special amino acids, seleno-cysteine and pyrolysine, there are a vast number of "nonstandard amino acids" which are not incorporated into protein in vivo. Examples of nonstandard amino acids include the sulfur-containing taurine and the neurotransmitters GABA and dopamine. Other examples are lanthionine, 2-Aminoisobutyric acid, and dehydroalanine. Further non standard amino are ornithine and citrulline.

Non-standard amino acids are usually formed through modifications to standard amino acids. For example, taurine can be formed by the decarboxylation of cysteine, while dopamine is synthesized from tyrosine and hydroxyproline is made by a posttranslational modification of proline (common in collagen). Examples of non-natural amino acids are those listed e.g. in 37 C.F.R. section 1.822(b)(4), all of which are incorporated herein by reference.

Both standard and non standard amino acid residues described herein can be in the "D" or or "L" isomeric form.

It is contemplated that a functional equivalent according to the invention may comprise any amino acid including non-standard amino acids. In preferred embodiments a functional equivalent comprises only standard amino acids.

The standard and/or non-standard amino acids may be linked by peptide bonds or by non-peptide bonds, however are in general linked only by peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Suitably variants will be at least 70% and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence of human RhoC.

Sequence identity can be calculated using a number of well-known algorithms and applying a number of different gap penalties. The sequence identity is calculated relative to full-length SEQ ID NO: 1. Any sequence alignment tool, such as but not limited to FASTA, BLAST, or LALIGN may be used for searching homologues and calculating sequence identity. Moreover, when appropriate any commonly known substitution matrix, such as but not limited to PAM, BLOSSUM or PSSM matrices may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Functional equivalents may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins, however it is preferred that the functional equivalent does not contain chemical modifications.

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art.

A functional homologue may be a deletion mutant of RhoC as identified by SEQ ID NO: 1 sharing at least 70% and accordingly, a functional homologue preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity.

MHC

There are two types of MHC molecules; MHC class I molecules and MHC class II molecules. MHC class I molecules are recognized by CD8 T-cells, which are the principal effector cells of the adaptive immune response. MHC class II molecules are mainly expressed on the surface of antigen presenting cells (APCs), the most important of which appears to be the dendritic cells. APCs stimulate naïve T-cells, as well as other cells in the immune system. They stimulate both CD8 T-cells and CD4 T-cells.

In one embodiment, there are provided novel MHC Class I-restricted peptide fragments consisting of 8-10 amino acids from RhoC of SEQ ID NO 1 or a functional homologue thereof, wherein at the most two amino acids of SEQ ID NO 1 have been substituted, which are characterised by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay may be carried out as described previously (WO 2005/049073, Example 1.2), and it is based on stabilisation of the HLA molecule after loading of peptide to the peptide transporter deficient cell line T2. Subsequently, correctly folded stable HLA heavy chains are immunoprecipitated using conformation dependent antibodies and the peptide binding is quantitated. The peptides of this embodiment comprises (or more preferably consists of) at the most 200, preferably at the most 100, more preferably at the most 50, yet more preferably at the most 25, even more preferably at the most 20, yet even more preferably at the most 15, such as at the most 10, for example in the range of 8 to 10 contiguous amino acids of RhoC of SEQ ID NO 1 or a functional homologue thereof wherein at the most two amino acids of SEQ ID NO 1 have been substituted.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

In another preferred embodiment, there are provided novel MHC Class II-restricted peptide fragments of RhoC of SEQ ID NO 1 or a functional homologue thereof, wherein at the most two amino acids of SEQ ID NO 1 have been substituted, (also referred to herein as "peptides"), which are characterised by having at least one of several features described herein below. The peptides of this embodiment comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 of SEQ ID NO 1 or a functional homologue thereof, wherein at the most two amino acids of SEQ ID NO 1 have been substituted, Thus there are provided novel MHC Class I-restricted peptide fragments of 8-10 amino acids or novel MHC Class II-restricted peptide fragments of 18-25 amino acids of RhoC of SEQ ID NO 1 or a functional homologue thereof, wherein at the most two amino acids of SEQ ID NO 1 have been substituted, (in conjunction referred to herein as "peptides") which are characterised by having at least one of several features described herein below, one of which is the ability to bind to the Class I or Class II HLA molecule to which it is restricted.

In particular embodiments there are provided peptide fragments, which is an MHC Class I-restricted peptide or an MHC class II-restricted peptide having at least one of the following characteristics:
 (i) capable of eliciting INF-γ-producing cells in a PBL population of a cancer patient at a frequency of at least 1 per $10^4$ PBLs as determined by an ELISPOT assay, and/or
 (ii) capable of in situ detection in a tumor tissue of CTLs that are reactive with the epitope peptide.
 (iii) capable of inducing the growth of RhoC specific T-cells in vitro.

More preferred peptides according to the present invention are peptides capable of raising a specific T-cell response as determined by an ELISPOT assay, for example the ELISPOT assay described in Example 1 herein below and in detail in WO 2005/049073 Example 1.4. Some peptides although not binding MHC class I or class II with high affinity still may give rise to a T-cell response as determined by ELISPOT. Other peptides capable of binding MHC class I or class II with high affinity also give rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 50 peptide specific spots per $10^8$ cells, more preferably per $10^7$, even more preferably per $10^6$, yet more preferably per $10^5$ cells, such as per $10^4$ cells are measured.

Most preferred peptides according to the present invention are peptides that are capable of eliciting a cellular immune response in a cancer patient.

As mentioned above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterised by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32(w19), HLA-Aw33(w19), HLA-Aw34(10), HLA-Aw36, HLA-Aw43, HLA-Aw66(10), HLA-Aw68(28), HLA-A69(28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24. In specific embodiment, the peptide of the invention is restricted a MHC Class I HLA species HLA-A2 or HLA-A3.

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments of the invention, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including but not limited to any of the following: HLA-Cw1, HLA-Cw2, HLA-Cw3, HLA-Cw4, HLA-Cw5, HLA-Cw6, HLA-Cw7 and HLA-Cw1.

In further useful embodiments, the peptide of the invention is a peptide, which is restricted by a MHC Class II HLA molecule including but not limited to any of the following: HLA-DPA-1, HLA-DPB-1, HLA-DQA1, HLA-DQB1, HLA-DRA, HLA-DRB and all alleles in these groups and HLA-DM, HLA-DO.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from the RhoC, which are likely to bind to the particular HLA molecule. Representative examples of such analyses for a range of HLA molecules are given in the below table:

| HLA allele | Position 1 | Position 2 | Position 3 | Position 5 | Position 6 | Position 7 | C-terminal |
|---|---|---|---|---|---|---|---|
| HLA-A1 |  | T, S | D, E |  |  | L | Y |
| HLA-A2 |  | L, M |  | V |  |  | L, V |
| HLA-A3 |  | L, V, M | F, Y |  |  |  | K, Y, F |
| HLA-A11 |  | V, I, F, Y | M, L, F, Y, I |  |  |  | K, R |
| HLA-A23 |  | I, Y |  |  |  |  | W, I |
| HLA-A24 |  | Y |  | I, V | F |  | I, L, F |
| HLA-A25 |  | M, A, T | I |  |  |  | W |
| HLA-A26 | E, D | V, T, I, L, F |  |  | I, L, V |  | Y, F |
| HLA-A28 | E, D | V, A, L |  |  |  |  | A, R |
| HLA-A29 |  | E |  |  |  |  | Y, L |
| HLA-A30 |  | Y, L, F, V |  |  |  |  | Y |
| HLA-A31 |  |  | L, M, F, Y |  |  |  | R |
| HLA-A32 |  | I, L |  |  |  |  | W |
| HLA-A33 |  | Y, I, L, V |  |  |  |  | R |
| HLA-A34 |  | V, L |  |  |  |  | R |
| HLA-A66 | E, D | T, V |  |  |  |  | R, K |
| HLA-A68 | E, D | T, V |  |  |  |  | R, K |
| HLA-A69 |  | V, T, A |  |  |  |  | V, L |
| HLA-A74 |  | T |  |  |  |  | V, L |
| HLA-B5 |  | A, P | F, Y |  |  |  | I, L |
| HLA-B7 | * | P |  |  |  |  | L, F |
| HLA-B8 |  |  | K | K, R |  |  | L |
| HLA-B14 |  | R, K |  |  |  |  | L, V |
| HLA-B15 (B62) |  | Q, L, K, P, H, V, I, M, S, T |  |  |  |  | F, Y, W |
| HLA-B17 |  |  |  |  |  |  | L, V |
| HLA-B27 |  | R |  |  |  |  | Y, K, F, L |
| HLA-B35 |  | P |  |  |  |  | I, L, M, Y |
| HLA-B37 |  | D, E |  |  |  |  | I, L, M |
| HLA-B38 |  | H | D, E |  |  |  | F, L |
| HLA-B39 |  | R, H |  |  |  |  | L, F |
| HLA-B40 (B60, 61) |  | E | F, I, V |  |  |  | L, V, A, W, M, T, R |
| HLA-B42 |  | L, P |  |  |  |  | Y, L |
| HLA-B44 |  | E |  |  |  |  | F, Y, W |
| HLA-B46 |  | M, I, L, V |  |  |  |  | Y, F |
| HLA-B48 |  | Q, K |  |  |  |  | L |
| HLA-B51 |  | A, P, G |  |  |  |  | F, Y, I, V |
| HLA-B52 |  | Q | F, Y |  |  |  | I, V |
| HLA-B53 |  | P |  |  |  |  | W, F, L |
| HLA-B54 |  | P |  |  |  |  |  |
| HLA-B55 |  | P |  |  |  |  | A, V |
| HLA-B56 |  | P |  |  |  |  | A, V |
| HLA-B57 |  | A, T, S |  |  |  |  | F, W, Y |
| HLA-B58 |  | A, T, S |  |  |  |  | F, W, Y |
| HLA-B67 |  | P |  |  |  |  | L |
| HLA-B73 |  | R |  |  |  |  | P |
| HLA-Cw1 |  | A, L |  |  |  |  | L |
| HLA-Cw2 |  | A, L |  |  |  |  | F, Y |
| HLA-Cw3 |  | A, L |  |  |  |  | L, M |

-continued

| HLA allele | Position 1 | Position 2 | Position 3 | Position 5 | Position 6 | Position 7 | C-terminal |
|---|---|---|---|---|---|---|---|
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

* In one embodiment there is no specific anchor residue for this position, however in a preferred embodiment the anchor residue is R or A.

Thus, as an example, nonapeptides potentially having the ability to bind to HLA-A3 would have one of the following sequences: Xaa-L-Y-Xaa-Xaa-Xaa-Xaa-Xaa-K, Xaa-L-Y-Xaa-Xaa-Xaa-Xaa-Xaa-Y; Xaa-L-Y-Xaa-Xaa-Xaa-Xaa-Xaa-F or Xaa-V-Y-Xaa-Xaa-Xaa-Xaa-Xaa-K (Xaa indicating any amino acid residue). In a similar manner, sequences potentially having the ability to bind to any other HLA molecule can be designed.

It will be appreciated that the person of ordinary skill in the art will be able to identify further "anchor residue motifs" for a given HLA molecule.

The immunogenically active peptide fragment may consist of a consecutive sequence of in the range of 2 to 100, such as 5 to 75, for example of 8 to 50, preferably in the range of 9 to 25 amino acids of said RhoC of SEQ ID no 1 or said functional homologue thereof having at least 70% identity to SEQ ID NO 1.

The peptides of the invention comprises (or more preferably consists of) at the most 200, preferably at the most 100, more preferably at the most 60, yet more preferably at the most 25, even more preferably at the most 20, yet even more preferably at the most 15, such as at the most 10, for example in the range of 8 to 10 contiguous amino acids of RhoC of SEQ ID NO 1 or a functional homologue thereof, wherein at the most three amino acids of SEQ ID NO 1 have been substituted.

In some embodiments the peptides of the invention comprise the sequence RXGLQVRKNK SEQ ID NO: 178, wherein X is selected from the group consisting of alanine and leucine and wherein said peptide fragment is at the most 200, preferably at the most 100, more preferably at the most 60, yet more preferably at the most 25, even more preferably at the most 20, yet even more preferably at the most 15, such as at the most 10, for example in the range of 8 to 10 contiguous amino acids of RhoC of SEQ ID NO 1 or a functional homologue thereof, wherein at the most three amino acids of SEQ ID NO 1 have been substituted.

Other peptides of the invention comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 of SEQ ID NO 1 or a functional homologue thereof having at least 70% identity to SEQ ID 1.

In some embodiments the peptides of the invention comprise the sequence RXGLQVRKNK SEQ ID NO: 178, wherein X is selected from the group consisting of alanine and leucine and wherein said peptide fragment is between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 of SEQ ID NO 1 or a functional homologue thereof having at least 70% identity to SEQ ID 1.

Other peptides of the invention comprises (or more preferably consists of) between 10 and 150, preferably between 12 and 120, more preferably between 15 and 75, yet more preferably between 20 and 70, even more preferably between 22 and 65, such as between 26 and 60 contiguous amino acids of RhoC of SEQ ID NO 1 of SEQ ID NO 1 or a functional homologue thereof having at least 70% identity to SEQ ID 1.

In some embodiments the peptides of the invention comprise the sequence RXGLQVRKNK SEQ ID NO: 178, wherein X is selected from the group consisting of alanine and leucine and wherein said peptide fragment is between 10 and 150, preferably between 12 and 120, more preferably between 15 and 75, yet more preferably between 20 and 70, even more preferably between 22 and 65, such as between 26 and 60 contiguous amino acids of RhoC of SEQ ID NO 1 of SEQ ID NO 1 or a functional homologue thereof having at least 70% identity to SEQ ID 1.

In specific embodiments the peptides of the invention comprises the sequence RXGLQVRKNK SEQ ID NO: 178, wherein X is selected from the group consisting of alanine and leucine and wherein said peptide fragment wherein said peptide fragment is at the most 200, preferably at the most 100, more preferably is at the most 60 amino acids in length.

In some aspects of the present invention, peptides RhoC-derived longer than 8 to 10 amino acids are provided. Peptides longer than 8 to 10 amino acids are processed by the proteasome to a shorter length for binding to HLA molecules. Thus, when administering a peptide longer than 8 to 10 amino acids the longer peptide is processed into a series of smaller peptides in the cytosol by the proteasome. In one specific embodiment the longer peptide may comprise the 20 most C-terminal peptides of RhoC ATRAGLQVRKNKRRRGCPIL (SEQ ID NO: 4). The C-terminal RhoC peptide may thus be processed into nona—and/or decapeptides by the proteasome.

An advantage of using a longer peptide that may be processed by the proteasome into a variety of different shorter peptides is that more HLA classes may be targeted with one peptide than one 8 to 10 amino acid peptide that is restricted to a particular HLA class.

In other embodiments of the invention the possible processed peptides derived from the C-terminal peptide of RhoC are provided.

In specific embodiments, the nonapeptide of the invention is an RhoC C-terminal derived peptide having a sequence selected from the following: ATRAGLQVR (SEQ ID NO: 11), TRAGLQVRK (SEQ ID NO: 12), RAGLQVRKN (SEQ ID NO: 13), AGLQVRKNK (SEQ ID NO: 14), GLQVRKNKR (SEQ ID NO: 15), LQVRKNKRR (SEQ ID NO: 16), QVRKNKRRR (SEQ ID NO: 17), VRKNKRRRG (SEQ ID NO: 18), RKNKRRRGC (SEQ ID NO: 19), KNKRRRGCP (SEQ ID NO: 20), NKRRRGCPI (SEQ ID NO: 21), and KRRRGCPIL (SEQ ID NO: 22), wherein at the most two amino acids have been substituted, for example at the most one amino acid have been substituted. Preferably no amino acids have been substituted.

In specific embodiments, the decapeptide of the invention is an RhoC C-terminal derived peptide having a sequence selected from the following: ATRAGLQVRK (SEQ ID NO: 23), TRAGLQVRKN (SEQ ID NO: 24), RAGLQVRKNK (SEQ ID NO: 25), AGLQVRKNKR (SEQ ID NO: 26), GLQVRKNKRR (SEQ ID NO: 27), LQVRKNKRRR (SEQ ID NO: 28), QVRKNKRRRG (SEQ ID NO: 29), VRKNKRRRGC (SEQ ID NO: 30), RKNKRRRGCP (SEQ ID NO: 31), KNKRRRGCPI (SEQ ID NO: 32) and NKRRRGCPIL (SEQ ID NO: 33), wherein at the most two amino acids have been substituted, for example at the most one amino acid have been substituted. Preferably no amino acids have been substituted.

In preferred embodiments the immunogenically active peptide fragment of the invention is selected from a sequence of RhoC of SEQ ID NO 1 or a functional homologue thereof), wherein at the most two amino acids have been substituted, that is different from the sequences of RhoA of SEQ ID NO 2 and RhoB of SEQ ID NO 3.

Thus, in one embodiment RhoC sequences that differ from RhoB are preferred. C-terminal RhoC sequences that differ from both RhoA and RhoB are most preferred. Suitably the peptides will differ from the sequences of RhoA of SEQ ID NO 2 and RhoB of SEQ ID NO 3 by seven amino acids, for example by six amino acids, such as by five amino acids, for example by four amino acids, such as by three amino acids, for example by two amino acids, such as by at least one amino acid.

Preferably the immunogenically active peptide fragment of the invention is different from the sequences of RhoA of SEQ ID NO 2 and RhoB of SEQ ID NO 3 by at least one amino acid. The preferred peptides of the invention may thus contain at least one of amino acid residues I43, Q123, R140, S141, S152, L157, E165, G178, V181, K183, N184, R186, R187, R188, P191 or I192 of RhoC of SEQ ID no 1.

Less preferably the peptides will differ from RhoB of SEQ ID NO 3 by seven amino acids, for example by six amino acids, such as by five amino acids, for example by four amino acids, such as by three amino acids, for example by two amino acids, such as by at least one amino acid. Thus the immunogenically active peptide fragment of the invention contains at least one of amino acid residues L81, M82, C83, F84, S85, I86, D87, S88, P89, D90, S91, L92, E93, N94, I95, K98, W99, T100, P101, E102, V103, K104, H105, F106, C107, P108, N109, P111, I112, I113, V115, G116, N117, K118, K119, T127, R129, E142, E143, D146, N149, F154, D155, G166, V167, R168, E169, V170, F171, E172, M173, A174, T175, R176, A177, L179, Q180, R182, K185, G189, C190.

Accordingly in a specific embodiment the immunogenically active peptide fragment of the invention consists of 50 amino acid residues, for example at the most 45 amino acid residues, such as at the most 40 amino acid residues, for example at the most 35 amino acid residues, such as at the most 30 amino acid residues, for example at the most 25 amino acid residues, such as 18 to 25 consecutive amino acids from RhoC of SEQ ID no 1 or a functional homologue thereof, wherein at the most three amino acids have been substituted and the peptide fragment contains at least one of the RhoC specific amino acid residues I43, Q123, R140, S141, S152, L157, E165, G178, V181, K183, N184, R186, R187, R188, P191 or I192 of RhoC of SEQ ID no 1.

Accordingly in another specific embodiment the immunogenically active peptide fragment of the invention consists of the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 consecutive amino acids from RhoC of SEQ ID no 1 or a functional homologue thereof, wherein at the most two amino acids have been substituted, wherein the peptide fragment contains at least one of the RhoC specific amino acid residues I43, Q123, R140, S141, S152, L157, E165, G178, V181, K183, N184, R186, R187, R188, P191 or I192 of RhoC of SEQ ID no 1.

Accordingly in another specific embodiment the immunogenically active peptide fragment of the invention consists of 100 amino acid residues, for example at the most 90 amino acid residues, such as at the most 80 amino acid residues, for example at the most 70 amino acid residues, such as at the most 65 amino acid residues, such as 26 to 60 consecutive amino acids from RhoC of SEQ ID no 1 or a functional homologue thereof, wherein at the most three amino acids have been substituted and the peptide fragment contains at least one of the RhoC specific amino acid residues I43, Q123, R140, S141, S152, L157, E165, G178, V181, K183, N184, R186, R187, R188, P191 or I192 of RhoC of SEQ ID no 1.

Accordingly in some embodiments the peptides of the invention are decapeptides selected from the group comprising the following: YVPTVFENYI (SEQ ID NO 34), VPTVFENYIA (SEQ ID NO 35), PTVFENYIAD (SEQ ID NO 36), TVFENYIADI (SEQ ID NO 37), VFENYIADIE (SEQ ID NO 38), FENYIADIEV (SEQ ID NO 39), ENYIADIEVD (SEQ ID NO 40), NYIADIEVDG (SEQ ID NO 41), YIADIEVDGK (SEQ ID NO 42), IADIEVDGKQ (SEQ ID NO 43), LVGNKKDLRQ (SEQ ID NO 44), VGNKKDLRQD (SEQ ID NO 45), GNKKDLRQDE (SEQ ID NO 46), NKKDLRQDEH (SEQ ID NO 47), KKDLRQDEHT (SEQ ID NO 48), DKLRQDEHTR (SEQ ID NO 170), KLRQDEHTRR (SEQ ID NO 50), LRQDEHTRRE (SEQ ID NO 51), RQDEHTRREL (SEQ ID NO 171), QDEHTRRELA (SEQ ID NO 172), LAKMKQEPVR (SEQ ID NO 54), AKMKQEPVRS (SEQ ID NO 55), KMKQEPVRSE (SEQ ID NO 56), MKQEPVRSEE (SEQ ID NO 57), KQEPVRSEEG (SEQ ID NO 58), QEPVRSEEGR (SEQ ID NO 59), EPVRSEEGRD (SEQ ID NO 60), PVRSEEGRDM (SEQ ID NO 61), VRSEEGRDMA (SEQ ID NO 62), RSEEGRDMAN (SEQ ID NO 63), SEEGRDMANR (SEQ ID NO 64), EGRDMANRIS (SEQ ID NO 65), GRDMANRISA (SEQ ID NO 66), RDMANRISAF (SEQ ID NO 67), DMANRISAFG (SEQ ID NO 68), MANRISAFGY (SEQ ID NO 69), ANRISAFGYL (SEQ ID NO 173), NRISAFGYLE (SEQ ID NO 71), RISAFGYLEC (SEQ ID NO 174), ISAFGYLECS (SEQ ID NO 73), SAFGYLECSA (SEQ ID NO 175), AFGYLECSAK (SEQ ID NO 75), FGYLECSAKT (SEQ ID NO 76), GYLECSAKTK (SEQ ID NO 77) YLECSAKTKE (SEQ ID NO 78), LECSAKTKEG (SEQ ID NO 79), ECSAKTKEGV (SEQ ID NO 80) CSAKTKEGVR (SEQ ID NO 81), SAKTKEGVRE (SEQ ID NO 82), AKTKEGVREV (SEQ ID NO 176), KTKEGVREVF (SEQ ID NO 157), TKEGVREVFE (SEQ ID NO 89) KEGVREVFEM (SEQ ID NO 86) EGVREVFEMA (SEQ ID NO 177), EVFEMATRAG SEQ ID NO 88), VFEMATRAGL (SEQ ID NO 89), FEMATRAGLQ (SEQ ID NO 90), EMATRAGLQV (SEQ ID NO 91), MATRAGLQVR (SEQ ID NO 92), ATRAGLQVRK (SEQ ID NO 93), TRAGLQVRKN (SEQ ID NO 94), RAGLQVRKNK (SEQ ID NO 10), AGLQVRKNKR (SEQ ID NO 96), GLQVRKNKRR (SEQ ID NO 97), LQVRKNKRRR (SEQ ID NO 98), QVRKNKRRRG (SEQ ID NO 99), VRKNKRRRGC (SEQ ID NO 100), RKNKRRRGCP (SEQ ID NO 101), KNKRRRGCPI (SEQ ID NO 102), NKRRRGCPIL (SEQ ID NO 103) or a functional homologue thereof, wherein at the most two amino acids have been substituted. Preferably no amino acids have been substituted.

Accordingly in some embodiments the peptides of the invention are nonapeptides selected from the group comprising the following: VPTVFENYI (SEQ ID NO 104), PTVFENYIA (SEQ ID NO 105), TVFENYIAD (SEQ ID NO 106), VFENYIADI (SEQ ID NO 107), FENYIADIE (SEQ ID NO 108), ENYIADIEV (SEQ ID NO 109), NYIADIEVD (SEQ ID NO 110), YIADIEVDG (SEQ ID NO 111), IADIEVDGK (SEQ ID NO 112), VGNKKDLRQ (SEQ ID NO 113), GNKKDLRQD (SEQ ID NO 114), NKKDLRQDE (SEQ ID NO 115), KKDLRQDEH (SEQ ID NO 116), KDLRQDEHT (SEQ ID NO 117), KLRQDEHTR (SEQ ID NO 118), LRQDEHTRR (SEQ ID NO 119), RQDEHTRRE (SEQ ID NO 120), QDEHTRREL (SEQ ID NO 121), AKMKQEPVR (SEQ ID NO 122), KMKQEPVRS (SEQ ID NO 123), MKQEPVRSE (SEQ ID NO 124), KQEPVRSEE (SEQ ID NO 125), QEPVRSEEG (SEQ ID NO 126), EPVRSEEGR (SEQ ID NO 127), PVRSEEGRD (SEQ ID NO 128), VRSEEGRDM (SEQ ID NO 129), RSEEGRDMA (SEQ ID NO 130), SEEGRDMAN (SEQ ID NO 131), GRDMANRIS (SEQ ID NO 132), RDMANRISA (SEQ ID NO 133), DMANRISAF (SEQ ID NO 134), MANRISAFG (SEQ ID NO 135), ANRISAFGY (SEQ ID NO 136), NRISAFGYL (SEQ ID NO 137), RISAFGYLE (SEQ ID NO 138), ISAFGYLEC (SEQ ID NO 139), SAFGYLECS (SEQ ID NO 140), AFGYLECSA (SEQ ID NO 141), FGYLECSAK (SEQ ID NO 142), GYLECSAKT (SEQ ID NO 144), YLECSAKTKE (SEQ ID NO 145), LECSAKTKEG (SEQ ID NO 146), ECSAKTKEGV (SEQ ID NO 147) CSAKTKEGVR (SEQ ID NO 148), SAKTKEGVRE (SEQ ID NO 149), KTKEGVREV (SEQ ID NO 150), KEGVREVFE (SEQ ID NO 152), EGVREVFEM (SEQ ID NO 153), VFEMATRAG (SEQ ID NO 154), FEMATRAGL (SEQ ID NO 155), MATRAGLQV (SEQ ID NO 157), ATRAGLQVR (SEQ ID NO 158), TRAGLQVRK (SEQ ID NO 159), RAGLQVRKN (SEQ ID NO 160), AGLQVRKNK (SEQ ID NO 161), GLQVRKNKR (SEQ ID NO 162), LQVRKNKRR (SEQ ID NO 163), QVRKNKRRR (SEQ ID NO 164), VRKNKRRRG (SEQ ID NO 165), RKNKRRRGC (SEQ ID NO 166), KNKRRRGCP (SEQ ID NO 167), NKRRRGCPI (SEQ ID NO 168), KRRRGCPIL (SEQ ID NO 169) or a functional homologue thereof, wherein at the most two amino acids have been substituted. Preferably no amino acids have been substituted.

In specific embodiment the peptides of the invention are selected from the following VYVPTVFENYIADIEVDGKQV (SEQ ID NO: 5), ILVGNKKLRQDEHTRRLAK (SEQ ID NO: 6) and ELAKMKQEPVRSEEGRDMANR (SEQ ID NO: 7), or a functional homologue thereof, wherein at the most three amino acids have been substituted, such as at the most two amino acids have been substituted, for example at the most one amino acid have been substituted. Preferably no amino acids have been substituted.

The C-terminal part of the sequence of RhoC of SEQ ID NO 1 is most different to the sequences of RhoA of SEQ ID NO 2 and RhoB of SEQ ID NO 3. In preferred embodiments of the invention the peptides may be selected from the C-terminal part of RhoC of SEQ ID NO 1.

Other peptides of the invention comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 or a functional homologue thereof having at least 70% identity to SEQ ID NO 1, wherein at the most two amino acids of RhoC of SEQ ID no 1 has been substituted, deleted or added.

In a preferred embodiment of the invention the peptide comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 or a functional homologue thereof, wherein at the most three amino acids have been substituted, deleted or added.

Other peptides of the invention comprises (or more preferably consists of) between 10 and 150, preferably between 12 and 120, more preferably between 15 and 75, yet more preferably between 20 and 70, even more preferably between 22 and 65, such as between 26 and 60 contiguous amino acids of RhoC of SEQ ID NO 1 or a functional homologue thereof having at least 70% identity to SEQ ID NO 1, wherein at the most two amino acids of RhoC of SEQ ID no 1 has been substituted, deleted or added.

In a preferred embodiment of the invention the peptide comprises (or more preferably consists of) between 10 and 150, preferably between 12 and 120, more preferably between 15 and 75, yet more preferably between 20 and 70, even more preferably between 22 and 65, such as between 26 and 60 contiguous amino acids of RhoC of SEQ ID NO 1 or a functional homologue thereof, wherein at the most three amino acids have been substituted, deleted or added.

In preferred embodiments of the invention the peptide comprises the sequence RXGLQVRKNK SEQ ID NO: 178, wherein X is selected from the group consisting of alanine and leucine and wherein said peptide fragment is at the most 60 amino acids in length.

In specific embodiment the peptides of the invention are selected from the C-terminal of RhoC, thus selected from the following EEGRDMANRISAFGYKECSAKTKEGVREVFEMATRAGLQVRKNKRRRGCPIL (SEQ ID NO: 8) or ATRAGLQVRKNKRRRGCPIL (SEQ ID NO: 4) or RAGLQVRKNK (SEQ ID NO: 10). In another preferred embodiment the peptide is RLGLQVRKNK (SEQ ID NO: 9) which is an artificial peptide, wherein the alanine of RAGLQVRKNK (SEQ ID NO: 10) has been substituted with leucine.

In an embodiment of the invention RhoC peptides comprise variant peptides. As used herein the expression "variant" refers to peptides which are homologous to the basic protein, which is suitably human RhoC, but which differs from the base sequence from which they are derived in that one or more amino acids within the sequence are substituted for other amino acids. Suitably variants will have at the most six amino acid substitutions, for example at the most five amino acid substitutions, such as at the most four amino acid substitutions, for example at the most three amino acid substitutions, such as at the most two amino acid substitutions, for example at the most one amino acid substitution.

Thus, in useful embodiments, the peptides of the invention include peptides, the sequences of which comprise, for each of the specific HLA alleles listed in the table, any of the amino acid residues as indicated in the table.

Thus, the peptides of the invention may be any of the above-mentioned peptides comprising contiguous sequences from RhoC, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in the table above.

A non-limiting example of how to prepare peptides of RhoC comprising anchor residues of a given HLA-A specific peptide is described in example 1 in the section "HLA-A3 binding peptides from RhoC". Thus, in one embodiment of the invention the peptide the peptide may be any peptide comprising at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of RAGLQVRKNK (SEQ ID NO: 10) or RLGLQVRKNK (SEQ ID NO: 11).

Thus, an approach to identify short peptides of the invention includes the following steps: selecting a particular HLA molecule, e.g. one occurring at a high rate in a given population, carrying out an alignment analysis as described above to identify "anchor residue motifs" in the Rho gene protein, isolating or constructing peptides of a suitable size that comprise one or more of the identified anchor residues and testing the resulting peptides for the capability of the peptides to elicit INF-γ-producing cells in a PBL population of a cancer patient at a frequency of at least 1 per $10^4$ PBLs as determined by an ELISPOT assay as described herein in Example 1 and in detail in WO 2005/049073, and/or (iii) the capability of the peptides to detect in situ in a tumour tissue CTLs that are reactive with the epitope peptides being tested.

The peptide of the invention is, as mentioned above, derived from RhoC of SEQ ID NO 1 or a fragment hereof. The protein from which the peptide can be derived can be any RhoC from any animal species in which the protein is expressed. In preferred embodiments, the starting protein is from a mammal species including a rodent species, rabbit and a primate species such as humans. Based on the sequence of the selected protein, the peptide of the invention is derived by any appropriate chemical or enzymatic treatment of the protein starting material that results in a peptide of a suitable size as indicated above, or it can be synthesised by any conventional peptide synthesis procedures with which the person of ordinary skills in the art is familiar.

The peptide of the invention may have a sequence which is a native sequence of the RhoC from which is derived. However, peptides having a higher affinity to any given HLA molecule may be derived from such a native sequence by modifying the sequence by substituting, deleting or adding at least one amino acid residue, e.g. on the basis of the procedure described above whereby anchor residue motifs in respect of the given HLA molecule are identified.

A significant feature of the peptide of the invention is its capability to recognise or elicit INF-γ-producing responder T cells, i.e. cytotoxic T cells (CTLs) that specifically recognise the particular peptide in a PBL population or tumour cells of a cancer patient (target cells). This activity is readily determined by subjecting PBLs or tumour cells from a patient to an ELISPOT assay as described in Example 1 and in detail in WO 2005/049073 and example 1. Prior to the assay, it may be advantageous to stimulate the PBL population or the tumour cells to be assayed by contacting the cells with the peptide to be tested. Preferably, the peptide is capable of eliciting or recognising INF-γ-producing T cells at a frequency of at least 1 per $10^4$ PBLs as determined by an ELISPOT assay as used herein. More preferably the frequency is at least 5 per $10^4$ PBLs, most preferably at least 10 per $10^4$ PBLs, such as at least 50 or 100 per $10^4$ PBLs.

The ELISPOT assay represents a strong tool to monitor RhoC peptide specific T-cell responses. A major implication of the findings herein is that the peptides of the invention may be expressed and complexed with HLA molecules on cancer cells. This renders these cancer cells susceptible to destruction by CTLs and emphasizes the potential usefulness of RhoC immunization to control the growth of metastasis. The presence of spontaneous CTL-responses in PBLs from melanoma patients to HLA-restricted RhoC derived peptide epitopes as described in Example 1 shows the immunotherapeutic potential of RhoC immunogenic peptides.

In an embodiment the peptide of the invention is capable of eliciting INF-γ-producing cells in a PBL population of a patient having a cancer disease where RhoC of SEQ ID no 1 or a functional homologue thereof having at least 70% identity to SEQ ID NO 1 is expressed.

In a preferred embodiment of the invention, the clinical condition is a cancer. The term "cancer" as used herein is meant to encompass any cancer, neoplastic and preneoplastic disease. Said cancer may for example be selected from the group consisting of; colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In a preferred embodiment the vaccine composition according to the invention is for the treatment of a cancer selected from the group of; melanoma, ovarian cancer or lung cancer.

In a very preferred embodiment the cancer disease is metastatic cancer, thus preferably the clinical condition is any of the aforementioned cancers, which is metastatic, even more preferably the clinical condition is selected from the group of; metastatic melanoma, metastatic ovarian cancer or metastatic lung cancer.

In addition to their capacity to elicit immune responses in PBL populations it is also contemplated that the peptides of the invention are capable of eliciting cytolytic immune responses in situ, i.e. in solid tumour tissues. This may for example be demonstrated by providing HLA-peptide complexes, e.g. being multimerised and being provided with a detectable label, and using such complexes for immunohistochemistry stainings to detect in a tumour tissue CTLs that are reactive with the epitope peptide of the invention. Accordingly, a further significant feature of the peptide of the invention is that it is capable of in situ detection in a tumour tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

The vaccine composition of the invention may comprise any of the aforementioned peptides. The vaccine composition of the invention comprises of a consecutive sequence of in the range of 2 to 100, such as 5 to 75, for example 8 to 50, preferably in the range of 9 to 25 amino acids of said RhoC of SEQ ID no 1 or said functional homologue thereof having at least 70% identity to SEQ ID NO 1. In a preferred embodiment the vaccine composition comprises a sequence of RhoC of SEQ ID NO 1 that is different from the sequences of RhoB of SEQ ID No 3 by at least one amino acid. In an even more preferred embodiment the vaccine composition comprises a sequence of RhoC of SEQ ID NO 1 that is different from the sequences of RhoA of SEQ ID NO 2 or RhoB of SEQ ID NO 3 by at least one amino acid.

In one embodiment the vaccine composition of the invention may comprise a peptide fragment consisting of at the most 50 amino acid residues, for example at the most 45 amino acid residues, such as at the most 40 amino acid residues, for example at the most 35 amino acid residues, such as at the most 30 amino acid residues, for example at the most 25 amino acid residues, such as 15 to 20 amino acid residues.

In another embodiment the vaccine composition of the invention may comprise a peptide fragment consisting of at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 amino acid residues.

In another embodiment the vaccine composition of the invention may comprise a peptide fragment consisting of at the most 100 amino acid residues, for example at the most 90 amino acid residues, such as at the most 80 amino acid residues, for example at the most 70 amino acid residues, such as at the most 65 amino acid residues, such as 26 to 60 amino acid residues.

In some embodiments the vaccine composition may comprise a peptide fragment in the range of 8 to 60 amino acids, preferably in the range of 8 to 20 amino acids, wherein at the most three, such as at the most two amino acids, for example at the most one amino acid has been substituted. The substitution may be semi-conservative or preferably the substitution is conservative.

As there is the largest sequence difference between RhoA, RhoB and RhoC in the C-terminal end of the proteins, in preferred embodiments the vaccine composition of the invention consists of a sequence selected from the 100 most C-terminal amino acids, for example the 75 most C-terminal amino acids, such as the 60 most C-terminal amino acids of RhoC of SEQ ID no 1 or a functional homologue thereof having at least 70% identity to SEQ ID NO 1.

In specific embodiments, the vaccine composition may comprise a RhoC C-terminal derived peptide having a sequence selected from the following: ATRAGLQVR (SEQ ID NO: 11), TRAGLQVRK (SEQ ID NO: 12), RAGLQVRKN (SEQ ID NO: 13), AGLQVRKNK (SEQ ID NO: 14), GLQVRKNKR (SEQ ID NO: 15), LQVRKNKRR (SEQ ID NO: 16), QVRKNKRRR (SEQ ID NO: 17), VRKNKRRRG (SEQ ID NO: 18), RKNKRRRGC (SEQ ID NO: 19), KNKRRRGCP (SEQ ID NO: 20), NKRRRGCPI (SEQ ID NO: 21), and KRRRGCPIL (SEQ ID NO: 22), wherein at the most two amino acids have been substituted, for example at the most one amino acid have been substituted. Preferably no amino acids have been substituted.

In specific embodiments, the vaccine composition may comprise a RhoC C-terminal derived peptide having a sequence selected from the following: ATRAGLQVRK (SEQ ID NO: 23), TRAGLQVRKN (SEQ ID NO: 24), RAGLQVRKNK (SEQ ID NO: 25), AGLQVRKNKR (SEQ ID NO: 26), GLQVRKNKRR (SEQ ID NO: 27), LQVRKNKRRR (SEQ ID NO: 28), QVRKNKRRRG (SEQ ID NO: 29), VRKNKRRRGC (SEQ ID NO: 30), RKNKRRRGCP (SEQ ID NO: 31), KNKRRRGCPI (SEQ ID NO: 32) and NKRRRGCPIL (SEQ ID NO: 33), wherein at the most two amino acids have been substituted, for example at the most one amino acid have been substituted. Preferably no amino acids have been substituted.

In other specific embodiments, the vaccine composition may comprise a peptide selected from the group comprising the following: YVPTVFENYI (SEQ ID NO 34), VPTVFENYIA (SEQ ID NO 35), PTVFENYIAD (SEQ ID NO 36), TVFENYIADI (SEQ ID NO 37), VFENYIADIE (SEQ ID NO 38), FENYIADIEV (SEQ ID NO 39), ENYIADIEVD (SEQ ID NO 40), NYIADIEVDG (SEQ ID NO 41), YIADIEVDGK (SEQ ID NO 42), IADIEVDGKQ (SEQ ID NO 43), LVGNKKDLRQ (SEQ ID NO 44), VGNKKDLRQD (SEQ ID NO 45), GNKKDLRQDE (SEQ ID NO 46), NKKDLRQDEH (SEQ ID NO 47), KKDLRQDEHT (SEQ ID NO 48), DKLRQDEHTR (SEQ ID NO 170), KLRQDEHTRR (SEQ ID NO 50), LRQDEHTRRE (SEQ ID NO 51), RQDEHTRREL (SEQ ID NO 171), QDEHTRRELA (SEQ ID NO 172), LAKMKQEPVR (SEQ ID NO 54), AKMKQEPVRS (SEQ ID NO 55), KMKQEPVRSE (SEQ ID NO 56), MKQEPVRSEE (SEQ ID NO 57), KQEPVRSEEG (SEQ ID NO 58), QEPVRSEEGR (SEQ ID NO 59), EPVRSEEGRD (SEQ ID NO 60), PVRSEEGRDM (SEQ ID NO 61), VRSEEGRDMA (SEQ ID NO 62), RSEEGRDMAN (SEQ ID NO 63), SEEGRDMANR (SEQ ID NO 64), EGRDMANRIS (SEQ ID NO 65), GRDMANRISA (SEQ ID NO 66), RDMANRISAF (SEQ ID NO 67), DMANRISAFG (SEQ ID NO 68), MANRISAFGY (SEQ ID NO 69), ANRISAFGYL (SEQ ID NO 173), NRISAFGYLE (SEQ ID NO 71), RISAFGYLEC (SEQ ID NO 174), ISAFGYLECS (SEQ ID NO 73), SAFGYLECSA (SEQ ID NO 175), AFGYLECSAK (SEQ ID NO 75), FGYLECSAKT (SEQ ID NO 76), GYLECSAKTK (SEQ ID NO 77) YLECSAKTKE (SEQ ID NO 78), LECSAKTKEG (SEQ ID NO 79), ECSAKTKEGV (SEQ ID NO 80) CSAKTKEGVR (SEQ ID NO 81), SAKTKEGVRE (SEQ ID NO 82), AKTKEGVREV (SEQ ID NO 176), KTKEGVREVF (SEQ ID NO 157), TKEGVREVFE (SEQ ID NO 89) KEGVREVFEM (SEQ ID NO 86) EGVREVFEMA (SEQ ID NO 177), EVFEMATRAG SEQ ID NO 88), VFEMATRAGL (SEQ ID NO 89), FEMATRA- GLQ (SEQ ID NO 90), EMATRAGLQV (SEQ ID NO 91), MATRAGLQVR (SEQ ID NO 92), ATRAGLQVRK (SEQ ID NO 93), TRAGLQVRKN (SEQ ID NO 94), RAGLQVRKNK (SEQ ID NO 10), AGLQVRKNKR (SEQ ID NO 96), GLQVRKNKRR (SEQ ID NO 97), LQVRKNKRRR (SEQ ID NO 98), QVRKNKRRRG (SEQ ID NO 99), VRKNKRRRGC (SEQ ID NO 100), RKNKRRRGCP (SEQ ID NO 101), KNKRRRGCPI (SEQ ID NO 102), NKRRRGCPIL (SEQ ID NO 103) or a functional homologue thereof, wherein at the most two amino acids have been substituted. Preferably no amino acids have been substituted.

In other specific embodiments, the vaccine composition may comprise a peptide selected from the group comprising the following: VPTVFENYI (SEQ ID NO 104), PTVFENYIA (SEQ ID NO 105), TVFENYIAD (SEQ ID NO 106), VFENYIADI (SEQ ID NO 107), FENYIADIE (SEQ ID NO 108), ENYIADIEV (SEQ ID NO 109), NYIADIEVD (SEQ ID NO 110), YIADIEVDG (SEQ ID NO 111), IADIEVDGK (SEQ ID NO 112), VGNKKDLRQ (SEQ ID NO 113), GNKKDLRQD (SEQ ID NO 114), NKKDLRQDE (SEQ ID NO 115), KKDLRQDEH (SEQ ID NO 116), KDLRQDEHT (SEQ ID NO 117), KLRQDEHTR (SEQ ID NO 118), LRQDEHTRR (SEQ ID NO 119), RQDEHTRRE (SEQ ID NO 120), QDEHTRREL (SEQ ID NO 121), AKMKQEPVR (SEQ ID NO 122), KMKQEPVRS (SEQ ID NO 123), MKQEPVRSE (SEQ ID NO 124), KQEPVRSEE (SEQ ID NO 125), QEPVRSEEG (SEQ ID NO 126), EPVRSEEGR (SEQ ID NO 127), PVRSEEGRD (SEQ ID NO 128), VRSEEGRDM (SEQ ID NO 129), RSEEGRDMA (SEQ ID NO 130), SEEGRDMAN (SEQ ID NO 131), GRDMANRIS (SEQ ID NO 132), RDMANRISA (SEQ ID NO 133), DMANRISAF (SEQ ID NO 134), MANRISAFG (SEQ ID NO 135), ANRISAFGY (SEQ ID NO 136), NRISAFGYL (SEQ ID NO 137), RISAFGYLE (SEQ ID NO 138), ISAFGYLEC (SEQ ID NO 139), SAFGYLECS (SEQ ID NO 140), AFGYLECSA (SEQ ID NO 141), FGYLECSAK (SEQ ID NO 142), GYLECSAKT (SEQ ID NO 144), YLECSAKTKE (SEQ ID NO 145), LECSAKTKEG (SEQ ID NO 146), ECSAKTKEGV (SEQ ID NO 147) CSAKTKEGVR (SEQ ID NO 148), SAKTKEGVRE (SEQ ID NO 149), KTKEGVREV (SEQ ID NO 150), KEGVREVFE (SEQ ID NO 152), EGVREVFEM (SEQ ID NO 153), VFEMATRAG (SEQ ID NO 154), FEMATRAGL (SEQ ID NO 155), MATRAGLQV (SEQ ID NO 157), ATRAGLQVR (SEQ ID NO 158), TRAGLQVRK (SEQ ID NO 159), RAGLQVRKN (SEQ ID NO 160), AGLQVRKNK (SEQ ID NO 161), GLQVRKNKR (SEQ ID NO 162), LQVRKNKRR (SEQ ID NO 163), QVRKNKRRR (SEQ ID NO 164), VRKNKRRRG (SEQ ID NO 165), RKNKRRRGC (SEQ ID NO 166), KNKRRRGCP (SEQ ID NO 167), NKRRRGCPI (SEQ ID NO 168), KRRRGCPIL (SEQ ID NO 169) or a functional homologue thereof, wherein at the most two amino acids have been substituted. Preferably no amino acids have been substituted.

In specific embodiments the vaccine composition may comprise a peptide that comprises the sequence RXGLQVRKNK SEQ ID NO: 178, wherein X is selected from the group consisting of alanine and leucine and wherein said peptide fragment wherein said peptide fragment is between 10 and 150, preferably between 12 and 120, more preferably between 15 and 75, yet more preferably between 20 and 70, even more preferably between 22 and 65, such as between 26 and 60 contiguous amino acids of RhoC of SEQ ID NO 1 of SEQ ID NO 1 or a functional homologue thereof having at least 70% identity to SEQ ID 1.

In specific embodiments the vaccine composition may comprise a peptide that comprises the sequence RXGLQVRKNK SEQ ID NO: 178, wherein X is selected from the group consisting of alanine and leucine and wherein said peptide fragment wherein said peptide fragment is at the most 200, preferably at the most 100, more preferably is at the most 60 amino acids in length.

In other specific embodiments the vaccine composition may comprise a peptide that comprises the sequence RXGLQVRKNK SEQ ID NO: 178, wherein X is selected from the group consisting of alanine and leucine and wherein said peptide fragment wherein said peptide fragment is between 4 and 120, preferably between 8 and 100, more preferably between 10 and 75, yet more preferably between 12 and 60, even more preferably between 15 and 40, such as between 18 and 25 contiguous amino acids of RhoC of SEQ ID NO 1 of SEQ ID NO 1 or a functional homologue thereof having at least 70% identity to SEQ ID 1.

In other specific embodiments the vaccine composition may comprise a peptide that comprises the sequence RXGLQVRKNK SEQ ID NO: 178, wherein X is selected from the group consisting of alanine and leucine and wherein said peptide fragment wherein said peptide fragment is at the most 200, preferably at the most 100, more preferably at the most 60, yet more preferably at the most 25, even more preferably at the most 20, yet even more preferably at the most 15, such as at the most 10, for example in the range of 8 to 10 contiguous amino acids of RhoC of SEQ ID NO 1 or a functional homologue thereof, wherein at the most three amino acids of SEQ ID NO 1 have been substituted.

In very specific embodiments, the vaccine composition may comprise a peptide selected from the group comprising the following: VYVPTVFENYIADIEVDGKQV (SEQ ID NO: 5), ILVGNKKLRQDEHTRRLAK (SEQ ID NO: 6) and ELAKMKQEPVRSEEGRDMANR (SEQ ID NO: 7), or a functional homologue thereof, wherein at the most three amino acids have been substituted, such as at the most two amino acids have been substituted, for example at the most one amino acid have been substituted. Preferably no amino acids have been substituted.

In other very specific embodiment the vaccine composition may comprise a peptide from the C-terminal of RhoC, thus selected from the following EEGRDMANRISAFGYKECSAKTKEGVREVFEMATRAGLQVRKNKRRRGCPIL (SEQ ID NO: 8) or ATRAGLQVRKNKRRRGCPIL (SEQ ID NO: 4) or RAGLQVRKNK (SEQ ID NO: 10). In another preferred embodiment the peptide is RLGLQVRKNK (SEQ ID NO: 9) which is an artificial peptide, wherein the alanine of RAGLQVRKNK (SEQ ID NO: 10) has been substituted with leucine.

It is contemplated that the vaccine composition of the invention is capable of eliciting an immune response against a cancer expressing RhoC of SEQ ID no 1 or a functional homologue thereof having at least 70% identity to SEQ ID NO 1, when administered to an individual suffering from a cancer expressing RhoC. In a preferred embodiment the cancer is a metastatic cancer. The vaccine composition of the invention is capable of eliciting the production in a vaccinated patient of effector T-cells having a cytotoxic effect against the cancer cells and/or inducing infiltration of antigen specific T-cells in tumor stroma in a subject.

The vaccine composition according to the present invention may comprise a nucleic acid encoding a protein belonging to the RhoC or an immunologically active peptide fragment thereof. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences. Construction of suitable vectors containing one or more of these components employs standard ligation techniques which are known to a person skilled in the art. The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector.

The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus*], and *Listeria*. In general, induction of immunity to the heterologous antigen HPV16 L1 or E7 could be shown, with strong CTL induction and tumor regression in mice.

The vector may furthermore also comprise nucleic acids encoding a T-cell stimulatory polypeptide.

The invention also relates to a kit-of-parts comprising
i) any of the vaccine compositions described herein and/or
ii) any of the proteins belonging to the rho gene family described herein and/or
iii) any of the peptide fragments of the proteins of ii) described herein and/or
iv) any of the nucleic acids encoding the proteins of ii) or the peptides of iii)
and a further anti-cancer agent.

The components of the kit-of-parts are preferably comprised in individual compositions, it is however comprised within the scope of the present invention that the components of the kit-of-parts all are comprised within the same composition. The components of the kit-of-parts may thus be administered simultaneously or sequentially in any order.

The anti-cancer agent may be an agent used in chemotherapy or gene therapy, immunostimulating substances or antibodies. The immunostimulating substances may for example be cytokines, such as cytokines selected from the group consisting of GM-CSF, type I IFN, interleukin 12 and interleukin 15. The antibody is preferably an immunestimulating antibody such as anti-CD40 or anti-CTLA-4 antibodies. The immunestimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

It is evident that the findings of the present invention provide the basis for therapeutic as well as diagnostic applications of the protein or the peptide fragment of the invention.

An important aspect the invention relates to cultivating RhoC specific T-cells in vitro and adoptive transfer of these to patients. Adoptive transfer means that the physician directly transfers the actual components of the immune system that are already capable of producing a specific immune response, into a patient.

It is one objective to the present invention to provide RhoC specific T-cells, which may be useful for example for adoptive transfer. Isolated T-cells comprising T-cell receptors capable of binding specifically to RhoC peptide/MHC class I or RhoC peptide/MHC class II complexes can be adoptively transferred to patients, said T-cells preferably being T-cells that have been expanded in vitro, wherein the RhoC peptide may be any of the RhoC peptides mentioned herein above. Methods of expanding T-cells in vitro are well known to the skilled person. The invention also relates to methods of treatment comprising administering T-cells comprising T-cell receptors capable of binding specifically to a MHC-restricted RhoC peptide complex to an individual, such as a human being suffering from a cancer disease, wherein the RhoC derived peptide may be any of the RhoC peptides mentioned herein above. The invention furthermore relates to use of T-cells comprising T-cell receptors capable of binding specifically to RhoC or peptide fragments thereof for the preparation of a medicament for the treatment of a cancer disease. Autologous T-cell transfer may be performed essentially as described in Walter et al., (1995).

In yet another embodiment, such T-cells could be irradiated before adoptive transfer to control proliferation in the patient. It is possible to genetically engineer the specificity of T cells by TCR gene transfer. This allows the transfer of T cells bearing RhoC peptide specificity into patients. In general, the use of T cells for adoptive immunotherapy is attractive because it allows the expansion of T cells in a tumor- or virus-free environment, and the analysis of T cell function prior to infusion. The application of TCR gene-modified T cells (such as T-cells transformed with an expression construct directing expressing of a heterologous TCR) in adoptive transfer has several advantages in comparison to the transfer of T cell lines. (i) the generation of redirected T cells is generally applicable. (ii) High-affinity or very high-affinity TCRs can be selected or created and used to engineer T cells. (iii) High-avidity T cells can be generated using codon optimized or murinized TCRs allowing better surface expression of the stabilized TCRs. Genetic engineering of T cell specificity by T cell receptor (TCR) gene transfer may be performed essentially as described in Morgan et al., (2006).

Accordingly, in a further aspect the present invention provides a vaccine composition comprising the protein or the peptide fragment of the invention, in particular a pharmaceutical composition which, when it is administered to a patient with metastatic cancer, is capable of eliciting an immune response against the cancer disease including eliciting the production in the vaccinated patient of effector T cells having a cytotoxic effect against the cancer cells.

As it is well known, that the different HLA molecules are of different prevalence in the major human populations, there is a requirement of identifying peptide epitopes restricted to several HLA class I molecules to extend the patient cohort that can be treated according to the methods of the present invention. The characterisation of multiple RhoC epitopes with different HLA restriction elements broadens the clinical potential of this target antigen in two important ways: (i) It increases the number of patients eligible for immunotherapy based on RhoC derived peptides. The HLA-A2 antigen is expressed by around 50% of the Caucasian and Asian populations, the HLA-A1 and HLA-A3 antigens are both expressed by around 25% of Caucasians and 5% of Asians, whereas the HLA-A11 antigen is expressed by around 15% of Caucasians and 30% of Asians. Even though these numbers cannot be added up due to co-expression, a combination of peptides restricted by a multiplicity of these would certainly encompass most cancer patients, (ii) The collective targeting of several restriction elements in each patient is likely to decrease the risk of immune escape by HLA-allele loss. Loss of a single HLA allele is a significant component of MHC alterations described for cancer cells, whereas total loss of Class I expression is a rather infrequent event. Thus, with the identification of RhoC epitopes restricted to different HLA alleles; it would be possible to target more than one HLA-molecule simultaneously in patients with allelic overlap. Also, with the cellular processing of the longer C-terminal RhoC peptide by the proteasome, it would be possible to target more than one HLA-molecule simultaneously in patients with allelic overlap The invention also relates to highly immunogenic multi-epitope vaccines. Preferably, such vaccines should be designed so as to facilitate a simultaneous delivery of the best-suited RhoC-derived peptides optionally in combination with other suitable peptides and/or adjuvants as described hereinafter. The present invention encompasses such multi-epitope vaccines comprising RhoC-derived peptides optionally in combination with further proteins or peptides fragments not belonging to or derived from RhoC and/or adjuvants as described hereinafter. An important factor driving the development of vaccines having a more complex composition is the desire to target multiple tumor antigens e.g. by designing vaccines comprising or encoding a collection of carefully selected CTL and $T_h$ cell epitopes. The invention thus in one aspect relates to vaccine compositions comprising both Class I and Class II-restricted RhoC epitopes.

The peptides of the present invention thus comprise both peptides in a short 'MHC-ready' form (class I restricted), and in a longer form requiring processing by the proteasome (class II restricted).

As the peptides of the invention are relatively small molecules it may be required in such compositions to combine the peptides with various materials such as adjuvants, to produce vaccines, immunogenic compositions, etc. Adjuvants, broadly defined, are substances which promote immune responses. A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. It has been proposed to use granulocyte-macrophage colony stimulating factor (GM-CSF), a well known cytokine, as an adjuvant (WO 97/28816).

The vaccine compositions according to the invention preferably comprise an adjuvant and/or a carrier. Examples of useful adjuvants and carriers are given herein below. Thus the protein belonging to the Rho gene protein family or peptide fragment thereof present in the composition can be associated with a carrier such as e.g. a protein or an antigen-presenting cell such as e.g. a dendritic cell (DC) capable of presenting to the Rho gene protein family or peptide fragment thereof to a T-cell.

Adjuvants are any substance whose admixture into the vaccine composition increases or otherwise modifies the immune response to the RhoC or peptide fragment thereof. Carriers are scaffold structures, for example a polypeptide or a polysaccharide, to which the RhoC or peptide fragment thereof is capable of being associated.

Adjuvants could for example be selected from the group consisting of: $AlK(SO_4)_2$, $AlNa(SO_4)_2$, $AlNH_4 (SO_4)$, silica, alum, $Al(OH)_3$, $Ca_3 (PO_4)_2$, kaolin, carbon, aluminum hydroxide, muramyl dipeptides, N-acetyl-muramyl-L-threo-nyl-D-isoglutamine (thr-DMP), N-acetyl-nornuramyl-L-ala-nyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum, Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazochinilines are yet another example of preferred adjuvants. The most preferred adjuvants are adjuvants suitable for human use. Liposomes are in general not useful adjuvants for the present invention, and preferably the vaccine compositions of the invention therefore do not comprise liposomes.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with either a non-metabolizable mineral oil, a metabolizable oil, or a mixture of the two. They are prepared for use as an emulsion with an aqueous solution comprising RhoC or peptide fragment thereof. The surfactant is mannide oleate. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

The well-known cytokine GM-CSF is another preferred adjuvant of the present invention. GM-CSF has been used as an adjuvant for a decade and may preferably be GM-CSF as described in WO 97/28816.

A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. Recently, it has been proposed to use granulocyte-macrophage colony stimulating factor (GM-CSF), a well known cytokine, as an adjuvant (WO 97/28816).

Desirable functionalities of adjuvants capable of being used in accordance with the present invention are listed in the below table.

TABLE 1

Modes of adjuvant action

| Action | Adjuvant type | Benefit |
| --- | --- | --- |
| 1. Immunomodulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes | Cytosolic processing of protein yielding correct class 1 restricted peptides |
|  | w/o emulsions for direct attachment of peptide to cell surface MHC-1 | Simple process if promiscuous peptide(s) known |
| 4. Targeting | Particulate adjuvants which bind immunogen. Adjuvants which saturate Kupffer cells | Efficient use of adjuvant and immunogen |
|  | Carbohydrate adjuvants which target lectin receptors on macrophages and DCs | As above. May also determine type of response if targeting selective |
| 5. Depot Generation | w/o emulsion for short term | Efficiency |
|  | Microspheres or nanospheres for long term | Potential for single-dose vaccine |

Source: Cox, J. C., and Coulter, A. R. (1997). Vaccine 15, 248-56.

A vaccine composition according to the present invention may comprise more than one different adjuvant. Furthermore, the invention encompasses a therapeutic composition further comprising any adjuvant substance including any of the above or combinations thereof. It is also contemplated that RHoC or peptide fragments thereof, and the adjuvant can be administered separately in any appropriate sequence.

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid presenting the protein belonging to the rho gene family or peptide fragments thereof to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

The choice of antigen in the vaccine composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule.

Alternatively, the antigen of interest is selected based on the prevalence of the various HLA phenotypes in a given population. As an example, HLA-A2 is the most prevalent phenotype in the Caucasian population, and therefore, a composition containing a peptide binding to HLA-A2 will be active in a large proportion of that population.

However, the composition of the invention may also contain a combination of two or more RhoC derived peptides, each interacting specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

The amount of the immunogenic peptide of the invention in the pharmaceutical composition may vary, depending on the particular application. However, a single dose of the peptide composition is preferably anywhere from about 10 µg to about 5000 µg, more preferably from about 50 µg to about 2500 µg such as about 100 µg to about 1000 µg. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilised forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In example 2 a non-limiting example of preparation of a vaccine composition according to the invention is given as well as a non-limiting example of administration of such as a vaccine. It will be appreciated by the person skilled in the art that the protocol may be easily adapted to any of the vaccine compositions described herein.

In a further embodiment of the invention, the pharmaceutical composition of the invention is useful for treating a cancer patient, where, during cancer progression in that patient, the cancer cells have developed a reduced susceptibility to a chemotherapeutically active anti-cancer drug and/or radiotherapy.

Additionally, the composition according to the present invention may be provided as a multiepitope vaccine comprising class I restricted epitope and class II restricted epitopes as defined hereinbefore.

The immunoprotective effect of the composition of the invention can be determined using several approaches e.g. as described in WO 97/28816, supra. A successful immune response may also be determined by the occurrence of DTH reactions after immunisation and/or the detection of antibodies specifically recognising the peptide(s) of the vaccine composition.

In preferred embodiments, the pharmaceutical composition of the invention is a vaccine composition. The pharmaceutical composition may thus be an immunogenic composition or vaccine capable of eliciting an immune response to a cancer disease. As used herein, the expression "immunogenic composition or vaccine" refers to a composition eliciting at least one type of immune response directed against cancer cells. Thus, such an immune response may be any of the types mentioned above: A CTL response where CTLs are generated that are capable of recognising the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response.

In useful embodiments an immunogenic response directed against a cancer disease is elicited by administering the peptide of the invention either by loading MHC class I or class II molecules on antigen presenting cells (APCs) from the patient, by isolating PBLs from the patient and incubating the cells with the peptide prior to injecting the cells back into the patient or by isolating precursor APCs from the patient and differentiating the cells into professional APCs using cytokines and antigen before injecting the cells back into the patient.

It is thus an aspect of the invention to provide vaccine compositions comprising antigen presenting cells comprising RhoC or an immunologically active peptide fragment thereof or a nucleic acid encoding said protein or said immunologically active peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with patients with different HLA type and different diseases.

Dendritic cells (DC) may be pulsed with 50 µg/ml HLA-restricted peptide (synthesized at GMP quality) for 1 h at 37° C. peptide and $5 \times 10^6$ cells are administered subcutaneously at day 1 and 14, subsequently every 4 weeks, additional leukapheresis after 5 vaccinations. The generation of DC for clinical use and quality control can be performed essentially as described in Nicolette et al., (2007).

Thus, in one embodiment of the present invention, a method for treating cancer patients is one wherein the peptide is administered by presenting the peptide to the patient's antigen presenting cells (APCs) ex vivo followed by injecting the thus treated APCs back into the patient. There are at least two alternative ways of performing this. One alternative is to isolate APCs from the cancer patient and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the patient. Another alternative way relies on the recent discoveries made in the field of dendritic cell biology. In this case, monocytes (being dendritic cell precursors) are isolated from the patient and differentiated in vitro into professional APC (or dendritic cells) by use of cytokines and antigen. Subsequently, the in vitro generated DCs are pulsed with the peptide and injected into the patient.

From the above description, the skilled person will readily realise that the proteins and/or peptides of the invention are useful as cancer diagnostic tools. Therefore, the peptides of the invention provide the basis for developing widely applicable diagnostic and prognostic procedures in respect of cancer diseases. Thus, in other useful embodiments the composition of the invention is a composition for ex vivo or in situ diagnosis of the presence in a cancer patient, e.g. based on the detection of RhoC reactive T cells among PBLs or in tumour tissue.

Accordingly, there is, in still further aspects, provided a diagnostic kit for ex vivo or in situ diagnosis of the presence in a cancer patient of RhoC reactive T cells among PBLs or in tumour tissue comprising one or more peptides of the invention, and a method of detecting in a cancer patient the presence of such reactive T cells, the method comprising contacting a tumour tissue or a blood sample with a complex of a peptide of the invention and a Class I or Class II HLA molecule or a fragment of such molecule and detecting binding of the complex to the tissue or the blood cells.

Another useful diagnostic or prognostic approach is based on generating antibodies in a heterologous animal species, e.g. murine antibodies directed against a human RhoC-derived peptide of the invention, which can then be used, e.g. to diagnose for the presence of cancer cells presenting the peptide. For such immunization purposes, the amount of peptide may be less than that used in the course of in vivo therapy, such as that mentioned above. In general, a preferred dose can range from about 1 µg to about 750 µg of peptide. It is also possible to produce monoclonal antibodies based on immunisation with a peptide of the invention. Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention. The invention furthermore relates to isolated T-cell receptors capable of binding specifically to a peptide or a protein of the invention as well as to isolated nucleic acids encoding same. Such T-cell receptors may for example be cloned from protein or peptide specific T-cells using standard techniques well known to the skilled person.

In one aspect the invention also relates to isolated T-cells comprising T-cell receptors capable of binding specifically to RhoC and/or peptide fragments thereof described herein. The isolated T-cells may be CD8 T-cells or CD4 T-cells. The isolated T-cells are preferably T-cells that have been expanded in vitro. Methods of expanding T-cells in vitro are well known to the skilled person. Such T-cells may in particular be useful in the treatment of cancer by adaptive transfer or autologous cell transfer. Thus, the invention also relates to pharmaceutical compositions comprising T-cells as well as methods of treatment comprising administering T-cells comprising T-cell receptors capable of binding specifically to RhoC or peptide fragments thereof to an individual, in need thereof such as a human being suffering from metatstatic cancer. The invention furthermore relates to use of T-cells comprising T-cell receptors capable of binding specifically to RhoC or peptide fragments thereof for the preparation of a medicament for the treatment of metastatic cancer. Autologous cell transfer may be performed essentially as described in Walter et al., (1995).

In one aspect, the invention provides a complex of a peptide of the invention and a Class I or Class II HLA molecule or a fragment of such molecule, which is useful as a diagnostic reagent such as it is described supra. Such a complex may be monomeric or multimeric.

The present invention provides the means for treating, preventing, alleviating or curing a clinical condition characterised by abnormal proliferation of cells, preferably a cancer, more preferably a metastatic cancer disease comprising administering to a patient suffering from the disease an effective amount of a composition as defined herein, a molecule that is capable of binding specifically to a peptide fragment, which may for example be an antibody or a T-cell receptor or the kit-of-parts described herein. Accordingly, it is a further aspect of the invention to provide a method of treating a metastatic cancer disease associated with the expression of a RhoC of SEQ ID NO 1.

In one aspect of the invention the vaccine composition is capable of eliciting a clinical response in subject. In one embodiment the clinical response may be characterised by a stable disease, in a preferred embodiment the clinical response may be characterised by a partial response or preferably the clinical response may be characterised by complete remission of a cancer disease. The clinical response may be determined as described herein below.

The disease according to the present invention may for example be a cancer disease selected from the group consisting of; colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer, wherein said cancer disease preferably is metastatic.

In a preferred embodiment the vaccine composition according to the invention vaccine composition is capable of eliciting a clinical response in subject, wherein the clinical response may be characterised by a stable disease, in a preferred embodiment the clinical response may be characterised by a partial response or preferably the clinical response may be characterised by complete remission of a cancer selected from the group of; melanoma, ovarian cancer or lung cancer, more preferably metastatic melanoma, ovarian cancer or lung cancer.

In another aspect of the invention the vaccine composition is capable of eliciting a clinical response in subject, wherein the clinical response is characterised by a decrease in the sum of the longest diameter of the largest target lesion. The decrease may be determined as described herein below.

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Evaluation of Target Lesions

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started Evaluation of Non-Target Lesions Complete Response (CR): Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions In some cases it will be appropriate to combine the treatment method of the invention with a further conventional cancer treatment such as chemotherapy, radiotheraphy, treatment with immunostimulating substances, gene therapy, treatment with antibodies and treatment using dendritic cells. Since elevated expression of RhoCs in tumour cells is correlated with drug resistance, the combination of a RhoC-based immunotherapy as disclosed by the present invention with cytotoxic chemotherapy might be an effective approach to treat cancer.

In one aspect the invention relates to methods of monitoring immunisation, said method comprising the steps of
i) providing a blood sample from an individual
ii) providing RhoC or a peptide fragment hereof, wherein said protein or peptide may be any of the proteins or peptides described herein
iii) determining whether said blood sample comprises antibodies or T-cells comprising T-cell receptors specifically binding the protein or peptide
iv) thereby determining whether an immune response to said protein or peptide has been raised in said individual.

The individual is preferably a human being, for example a human being that has been immunised with RhoC or a peptide fragment hereof or a nucleic acid encoding said protein or peptide.

DESCRIPTION OF DRAWINGS

FIG. 1. Alignment of RhoC, RhoA and RhoB.

Sequence alignments of Human RhoC, Human RhoA and Human RhoB.

Figure 2:
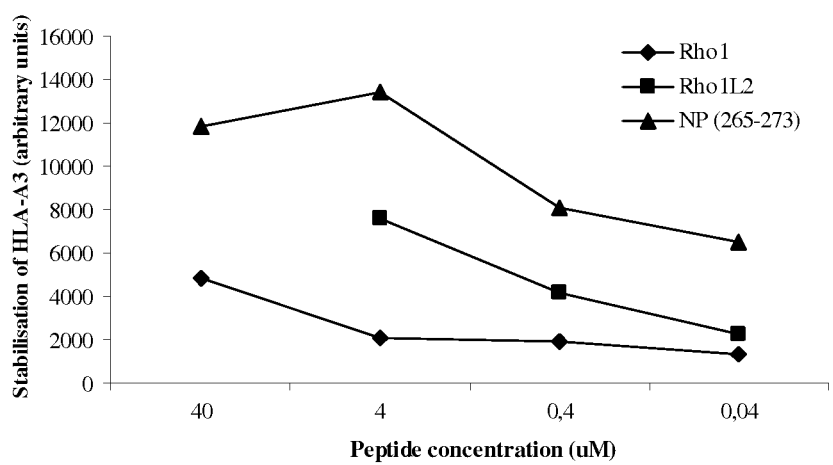

FIG. 2. Binding affinity of Rho1 and Rho1L2.

Stabilization of Rho1 and Rho1L2 was analyzed by assembly assay. Class I MHC heavy chain bands were quantified on a Phosphorimager. The amount of stabilized HLA-A3 heavy chain is directly related to the binding affinity of the added peptide. The binding of the HLA-A3-restricted positive control peptide Influenza $NP_{265-273}$ was compared with the peptide Rho1L2 and the native peptide Rho1.

Figure 3:
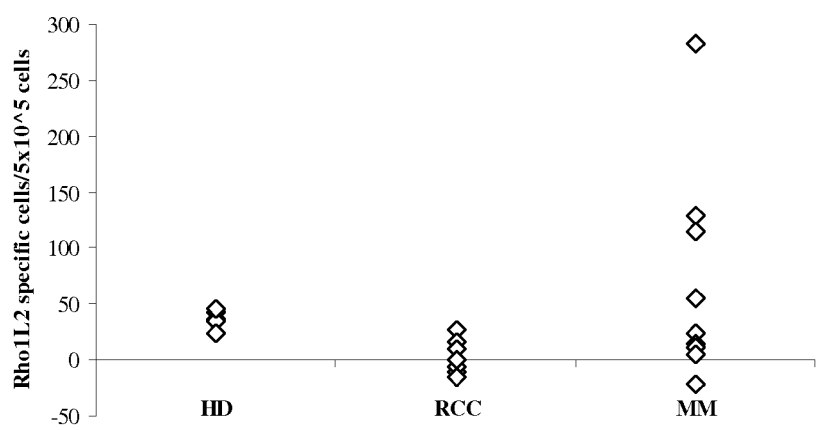

FIG. 3. HLA-A3 restricted T-cell responses against Rho1L2 as measured by IFN-γ ELISPOT.

The average number of peptide specific IFN-γ spots formed in response to Rho1L2 among $5\times10^5$ in vitro stimulated PBMC from five HLA-A3$^+$ healthy donors (HD), PBL from 10 Renal Cell Carcinoma patients (RCC), and 10 Melanoma patients (MM). Measurements were made in triplicates. The number of antigen-specific spots was calculated by subtracting the mean number of spots of the control wells from the mean number of spots in the positive wells; in order to prevent that replicates with a high standard variation are accepted as positive results, all replicates were analyzed by Student t-test for unpaired samples, results with a p-value <0.05 were considered as positive.

Figure 4:
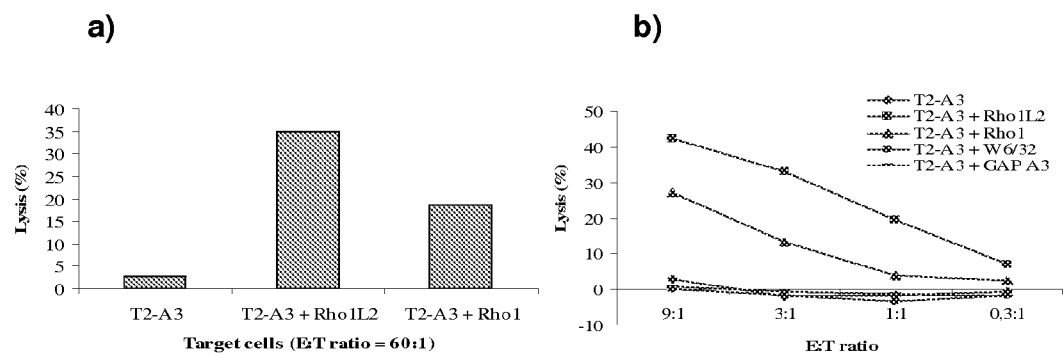

FIG. 4. T-cell antigen specificity and cross reactivity

Cytotoxicity by $^{51}$Cr-release assay of a bulk culture stimulated with Rho1L2-loaded autologous DC/autologous PBL. Specific lysis of T2-A3 cells with no peptide or pulsed with Rho1L2 or Rho1. E:T ratio=60:1, measurements were made in duplicates. a) Specificity of a T-cell clone (clone 9) assayed by $^{51}$Cr-release assay. Lysis of T2-A3 cells with no peptide, pulsed with Rho1L2, Rho1 or with the HLA-class I specific antibody W6/32 or HLA-A3 specific antibody GAP A3 at different E:T ratios (9:1; 3:1; 1:1; 0.3:1).

FIG. 5. Functional capacity of RhoC specific T cells a) Cytotoxicity of a bulk culture stimulated with Rho1L2-loaded autologous DC/autologous PBL. Specific lysis of the HLA-A3$^+$ melanoma cell line FM3 without and with the addition of the HLA-class I specific antibody W6/32.

b) Lysis by a Rho1L2 specific clone of the HLA-A3$^+$ melanoma cell line FM3, cell lysis with addition of unlabeled T2-A3 cells pulsed with Rho1L2 or no peptide (inhibitor to target ratio=20:1), and cell lysis of the HLA-A3$^+$ melanoma cell line FM9 and the HLA-A3$^-$ melanoma cell line FM82. Measurements were made in duplicates for all E:T ratios.

c) Lysis by a Rho1L2 specific clone of the HLA-A3$^+$ breast cancer cell line BT-20, colon cancer cell line HT-29 and head and neck cancer cell line CRL-2095. Measurements were made in duplicates for all E:T ratios.

EXAMPLES

Example 1

Immune Responses against RhoC

1. Patients

Peripheral blood lymphocytes (PBL) from HLA-A3$^+$ cancer patients or peripheral blood mononuclear cells (PBMC) from healthy controls were obtained from the University Hospital Herlev, Denmark. Cells were cryopreserved in FCS with 10% DMSO. Tissue typing was conducted at the Department of Clinical Immunology, The State Hospital, Copenhagen, Denmark. Informed consent was obtained from the patients before any of these measures.

2. Assembly Assay for Peptide Binding to MHC Class I Molecules

The binding affinity of the synthetic peptides (Genscript, Scotch Plains, US) to HLA-A3 molecules was measured by means of the assembly assay as described (13). The assay is based on the stabilization of the class I molecule after loading of different concentrations of peptide to the TAP-deficient cell line T2-A3. Briefly, T2-A3 cells were incubated in methionine-free RPMI 1640 (Gibco BRL, Paisley, UK) with 10% dialysed FCS. Subsequently, cells were metabolically labelled with 50 µCi $^{35}$S-methionine (Amersham, Birkeroed, Denmark). After incubation, cells were lysed in lysis buffer in the presence of protease inhibitors (100 µg/mliodoacetamide, 200 µg/ml PEFA block and 2 µg pepstatin (Roche diagnostics, Hvidovre, Denmark)) and with peptide in varying concentrations (4-0.04 µM). Cell nuclei were removed by ultracentrifugation. The supernatant of T2-A3 cells was heated for 5 min at 45° C. in order to reduce background signals by preferentially destabilizing empty HLA-A3. The samples were precleared by addition of Pansorbin (Calbiochem, Darmstadt, Germany) and left on rotation overnight. Stably folded HLA molecules were immune-precipitated using the HLA class I-specific, conformation-dependent mAb W6/32. A-Sepharose beads were added to collect the folded MHC complexes and separated by isoelectric focusing gel electropheresis. MHC heavy chains were quantified using the ImageGauge Phosphorimager program (FUJI Photo Film). The intensity of the band is directly related to the amount of peptide-bound class I MHC complex recovered during the assay. Subsequently, the extent of stabilization of HLA-A3 is directly related to the binding affinity of the added peptide. The $C_{50}$-value was calculated for each peptide as the peptide concentration sufficient for half maximal stabilization.

3. Ag Stimulation of PBL

To extend the sensitivity of the ELISPOT assay, PBL were stimulated once before analysis. At day 0, PBL were thawed and plated in 24-well plates (Nunc, Roskilde, Denmark) in X-Vivo medium (Cambrex Bio Science Copenhagen, Vallensbaek Strand, Denmark) with 5% heat-inactivated human serum in the presence of 10 µM peptide (GenScript, Scotch Plains, US). The following day 20 U/ml IL-2 (PeproTech, London, UK) was added to the cultures. The cultured cells were tested for reactivity in the ELISPOT on day 8.

4. Interferon-Gamma (INF-Gamma ELISPOT Assay)

The ELISPOT assay was used to quantify peptide epitope-specific INF-γ releasing effector cells as described previously (WO 2005/049073, Example 1.2). Briefly, nitrocellulose bottomed 96-well plates (MultiScreen MAIP N45, Millipore, Hedehusene, Denmark) were coated with anti-IFN-γ antibody (1-D1K, Mabtech, Nacka, Sweden). The wells were washed, blocked with X-vivo medium before adding $10^4$ stimulator T2-A3 cells (with or without 10 µM peptide; Rho1L2: RLGLQVRKNK; Rho1: RAGLQVRKNK (GenScript, Scotch Plains, US)) and effector cells at different concentrations. The plates were incubated overnight. The following day, medium was discarded and the wells were washed prior to addition of biotinylated secondary antibody (7-B6-1-Biotin, Mabtech, Nacka, Sweden). The plates were incubated for 2 hrs, washed and Avidin-enzyme conjugate (AP-Avidin, Calbiochem, Life Technologies, Inc., Roskilde, Denmark) was added to each well. Plates were incubated at RT for 1 hr before the enzyme substrate NBT/BCIP (Gibco Life Technology, Taastrup, Denmark) was added to each well and incubated at RT for 5-10 min. The reaction was terminated with tap-water upon the emergency of dark purple spots. The spots were counted using the ImmunoSpot® Series 2.0 Analyzer (CTL Analyzers, LLC, Cleveland, US) and the peptide specific CTL frequency could be calculated from the numbers of spot-forming cells. The number of antigen-specific spots was calculated by subtracting the mean number of spots of the control wells from the mean number of spots in the positive wells; responses with a p-value<0.05 (Student t-test for unpaired samples) were considered as positive. The definition is in respect with the CIMT Monitoring Panel inter-laboratory testing project (www.c-imt.org).

5. Dendritic Cells (DC)

DC were generated from PBMC by adherence on culture dishes at 37° C. for 60 min in RPMI-1640 enriched with 10% human AB serum. Adherent monocytes were cultured in RPMI-1640 supplemented with 10% human AB serum in the presence of IL-4 (1000 U/ml) and GM-CSF (800 U/ml) for 6 days. DC were matured by addition of IL-1β (2 ng/ml), IL-6 (1000 U/ml), TNF-α (10 ng/ml), and PGE$_2$ (1 µg/ml). Next day the resulting mature DC were pulsed with 10 µM peptide for 2 hrs at 37° C., irradiated (20 Gy) and $1 \times 10^5$ DC/ml were used for stimulation of $1 \times 10^6$ PBL/ml in the presence of 40 U/ml IL-2. IL-2 was added every 3-4 days.

6. Establishment of Antigen Specific T-Cell Cultures and Clones

PBL from a melanoma (MM) patient were stimulated with irradiated (20 Gy) autologous Rho1L2-loaded DC (PBL:DC ratio=$3 \times 10^6$:$3 \times 10^5$). The following day 120 U/ml IL-2 (PeproTech, London, UK) was added. Stimulation of the cultures were carried out every 10 days with Rho1L2-loaded irradiated autologous DC (2×) followed by Rho1L2-loaded irradiated autologous PBL (3×). Hundred and twenty U/ml IL-2 (PeproTech, London, UK) was added after each stimulation. After one month growing cultures were tested for specificity for Rho1L2.

PBL from a specific culture were cloned by limiting dilution in the presence of cloning mix containing $10^6$/ml irradiated (20 Gy) lymphocytes from three healthy donors in X-vivo with 5% heat-inactivated human serum, 25 mM HEPES buffer (GibcoBRL, Paisley, UK), and 120 U/ml IL-2 (PeproTech, London, UK). The plates were incubated at 37° C./5% CO$_2$. Every 3-4 days 50 µl fresh media were added containing IL-2 to a final concentration of 120 U/ml. Growing clones were expanded using cloning mix cells ($5 \times 10^4$ cells/well) and IL-2. After expansion the clones were tested for specificity and cytotoxic potential in a standard $^{51}$Cr-release assay.

7. Cytotoxicity Assay

Conventional $^{51}$Cr-release assays for CTL-mediated cytotoxicity were carried out as described elsewhere (Andersen et al., (1999) J Immunol 163:3812-3818). Target cells were T2-A3 cells, the HLA-A3$^+$ breast cancer cell line BT-20, the HLA-A3$^+$ colon cancer cell line HT-29, the HLA-A3$^+$ head and neck cancer cell line CRL-2095 (all available at the American Type Culture Collection (ATCC)), the HLA-A3$^+$ melanoma cell line FM9, the HLA-A3$^-$ melanoma cell line FM82, and the HLA-A3$^+$ melanoma cell line FM3 (Kirkin et al., (1995) Cancer Immunol Immunother 41: 71-81), with or without added HLA specific mAb W6/32 (Barnstable et al., (1978) Cell 14: 9-20) (2 µg/100 µl) (Schmidt et al., (2003) Blood 102: 571-576) or the HLA-A3 specific antibody GAPA3 (Sire et al., (1988) 140: 2422-2430).

Results

HLA-A3 Binding Peptides from RhoC

RhoC mainly differs from RhoA and RhoB in the C-terminal part of the sequence. Hence, this 20 amino acid region was scrutinized for putative HLA epitopes using the main HLA specific anchor residues as described herein above. We identified a possible HLA-A3 restricted peptide Rho1 (RAGLQVRKNK). However, as Alanine is a poor anchor amino acid in position 2 this peptide was only expected to bind to HLA-A3 with low affinity. As many of the established T-cell epitopes presented by cancer cells such as the melanoma antigens gp100 and MART-1 have relatively low binding affinities to the respective HLA class I molecules, it is common practice to generate heteroclitic peptides from such low-affinity epitopes by substitution of amino acids at specific positions, i.e., the anchor positions, which are crucial for the binding of the peptide to the HLA molecule (Pardoll D M (1998) Nat Med 4: 525-531; Scheibenbogen C., et al, (2002) Int J Cancer 98: 409-414). Consequently, we included a modified counterpart Rho1L2 (RLGLQVRKNK) in our studies, in which position 2 was modified from Alanine to Leucine. The two peptides were synthesized and examined for binding to HLA-A3 by comparison with the HLA-A3 high affinity positive control epitope from Influenza NP$_{265-273}$ (ILRGSVAHK) by the assembly assay (FIG. 2). The peptide concentration required for half maximal recovery of class I MHC molecules ($C_{50}$ value) was 0.3 µM for the Influenza NP$_{265-273}$ (FIG. 2). The modified Rho1L2 peptide bound with intermediate affinity ($C_{50}$=4), whereas the native peptide Rho1 only bound very weakly to HLA-A3 ($C_{50}$>40).

Spontaneous T-Cell Responses Towards RhoC

We scrutinized PBL from HLA-A3+ MM and renal cell carcinoma (RCC) patients for the presence of specific T-cell responses against the modified Rho1L2 (RLGLQVRKNK) peptide by means of the ELISPOT IFN-γ secretion assay. As depicted in FIG. 3, specific T-cell responses were present among PBL of 3 out of 10 MM patients. No responses were detected in either RCC patients or healthy controls (HD) against either Rho1L2 or Rho1.

T-Cell Antigen Specificity and Rho1/Rho1L2 Cross Reactivity

Having identified patients hosting responses against the Rho1L2 peptide, we used PBL from these cancer patients to generate CTL bulk cultures against this peptide in vitro. Subsequently, we in vitro stimulated PBL from such a patient with Rho1L2-pulsed autologous DC. After four in vitro restimulations, the peptide specificity was tested in standard $^{51}$Cr release assays using T2-A3 cells without peptide or loaded with Rho1 or Rho1L2 as target cells (FIG. 4a). This assay revealed that the bulk cultures lysed both T2-A3 cells pulsed with Rho1L2 and Rho1 efficiently, whereas no cytotoxicity was observed against unpulsed T2-A3 cells.

Next, CTL clones were established from these specific T-cell cultures by limiting dilution. After a short expansion step, the specificity of the growing clones was analyzed in standard $^{51}$Cr release assays. The data presented describe the results obtained for one growing clone (clone 9(*)). This clone effectively lysed T2-A3 cells pulsed with both the modified Rho1L2 and the native Rho1 peptide underlining that Rho1L2 specific T cells cross react with the native analogue peptide (FIG. 4b). To examine the HLA restriction of clone 9, we tested the effect of blocking HLA-class I by addition of the HLA specific mAb W6/32 and the HLA-A3 specific mAb GAP A3. Lysis could be completely blocked by incubation of the target cells with both antibodies (FIG. 4b).

Capacity of RhoC Specific T Cells to Kill Tumor Cells

First we examined the Rho1L2/Rho1 specific bulk cultures capacity to kill melanoma cells. To this end, the HLA-A3+ FM3 melanoma cells were killed with high efficacy in a HLA-restricted matter as lysis could be completely blocked by incubation of FM3 target cells with W6/32 (FIG. 5a).

Likewise clone 9 generated from the specific bulk culture was able to kill FM3 melanoma cells (FIG. 5b). The addition of cold (unlabeled) T2-A3 cells pulsed with the Rho1L2 peptide completely abrogated the killing of FM3 melanoma cells (FIG. 5b). Moreover, the RhoC specific CTL clone was able to lyse the HLA-A3+ melanoma cancer cell line FM9. As an additional control, we used the HLA-A3− melanoma cell line FM82 as target cells. No cytotoxicity was observed against this cell line. As the expression of RhoC in metastatic cancer has been described in cancers of different origin we further examined the RhoC specific CTL clone capacity to kill other cancer cells than melanoma. Subsequently, the HLA-A3+ breast cancer cell line BT-20, the HLA-A3+ head and neck cancer cell line CRL-2095 and the HLA-A3+ colon cell line HT-29 were used as target cells. The RhoC specific CTL clone lysed all HLA-A3+ cell lines, although the colon cell line HT-29 only to a limited extent.

Example 2

Non-Limiting Example of Preparation of a Vaccine Composition and Non-Limiting Example of Administration of Vaccine Peptide Vaccine RhoC peptides can e.g. be synthesized e.g. at the UVA Biomolecular Core Facility with a free amide NH$_2$ terminus and free acid COOH terminus. Each is provided as a lyophilized peptide, which is then reconstituted in sterile water and diluted with Lactated Ringer's solution (LR, Baxter Healthcare, Deerfield, Ill.) as a buffer for a final concentration of 67-80% Lactated Ringer's in water. These solutions are then sterile-filtered, placed in borosilicate glass vials, and submitted to a series of quality assurance studies including confirmation of identity, sterility, general safety, and purity, in accordance with FDA guidelines, as defined in IND 6453.

In practical circumstances, patients will receive a vaccine comprising about 100 μg of a class I HLA-restricted peptide or a class II HLA-restricted peptide or a combination of both. The patients are vaccinated with e.g. about 100 μg of the class I HLA peptide in adjuvant alone, or are vaccinated with 100 μg of the class II HLA peptide in adjuvant alone or are vaccinated with e.g. about 100 μg of the HLA class I-restricted peptide plus 190 μg of the class II-restricted peptide. The higher dose of the Class II peptide in the combination is calculated to provide equimolar quantities of the helper and cytotoxic epitopes. Additionally, patients can be vaccinated with a longer peptide comprising the amino acid sequences of both peptides.

The above peptides, in 1-ml aqueous solution, can be administered either as a solution/suspension with about 100 μg of QS-21, or as an emulsion with about 1 ml of Montanide ISA-51 adjuvant.

Patients are immunized e.g. at day 0 and months 1, 2, 3, 6, 9, and 12, with the peptides plus adjuvant, for a total of seven immunizations. With rare exceptions, the vaccinations are administered to the same arm with each vaccine. The peptides are preferably administered s.c.

REFERENCE LIST

Abecassis et al., RhoA induces MMP-9 expression at CD44 lamellipodial focal complexes and promotes HMEC-1 cell invasion. Exp Cell Res. 2003 Dec. 10; 291(2):363-76

Allal, C., et al., RhoA prenylation is required for promotion of cell growth and transformation and cytoskeleton organization but not for induction of serum response element transcription J. Biol. Chem. 2000, 275:31001

Andersen M H., Bonfill J E., Neisig A., Arsequell G., Sondergaard I., Valencia G et al., (1999) "Phosphorylated peptides can be transported by TAP molecules, presented by MHC molecules and recognized by phosphopeptide-specific CTL" J Immunol 163:3812-3818

Barnstable C J., Bodmer W F., Brown G., Galfre G., Milstein C., Williams A F., et al., (1978) "Production of monoclonal antibodies to group-A erythrocytes" Cell 14: 9-20

Bishop, A. L., Hall, A., Rho GTPases and their effector proteins, Biochem. J. 2000, 348 (Pt. 2):241

Clark E A, Golub T R, Lander E S, Hynes R O. Genomic analysis of metastasis reveals an essential role for RhoC. Nature. 2000 Aug. 3; 406(6795):532-5

Horiuchi A, Imai T, Wang C, Ohira S, Feng Y, Nikaido T, Konishi I. Up-regulation of small GTPases, RhoA and RhoC, is associated with tumor progression in ovarian carcinoma. Lab Invest. 2003 June; 83(6):861-70

Kirkin A F., Reichert Petersen T., Olsen A C., Li L., Straten P., Zeuten J., et al., (1995) "Generation of human-melanoma specific T lymphocyte clones defining novel cytolytic target with panels of newly established melanoma cell lines" Cancer Immunol Immunother 41: 71-81

Kleer C G, van Golen K L, Zhang Y, Wu Z F, Rubin M A, Merajver S D. Characterization of RhoC expression in benign and malignant breast disease: a potential new marker for small breast carcinomas with metastatic ability. Am J Pathol. 2002 February; 160(2):579-84

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science 2006; 314(5796):126-129.

Nicolette C A, Healey D, Tcherepanova I, Whelton P, Monesmith T, Coombs L, Finke L H, Whiteside T, Miesowicz F. Dendritic cells for active immunotherapy: optimizing design and manufacture in order to develop commercially and clinically viable products. Vaccine. 2007 Sep. 27; 25 Suppl 2:B47-60. Epub 2007 Jun. 21

Pardoll D M (1998) "Cancer vaccines" Nat Med 4: 525-531

Scheibenbogen C., Sun Y., Keilholz U., Song M., Stevanovic S., Asemissen A M., et al, (2002) "Identification of known and novel immunogenic T-cell epitopes from tumor antigens recognized by peripheral blood T cels from patients responding to IL-based treatment" Int J Cancer 98: 409-414

Schmidt S M, Schag K., Muller M R., Weck M M., Appel S., Kanz L., et al., (2003) "Survivin is a shared tumor-associated antigen expressed in a broad variety of malignancies and recognized by specific cytotoxic T cells" Blood 102: 571-576)

Shao, F., Dixon, J. E., YopT is a cysteine protease cleaving Rho family GTPases. Adv. Exp. Med. Biol. 2003, 529:79

Sire J., Chimini G., Boretto J., Toubert A., Kahnperles B., Layet C., et al., (1988) "Hybrid genes between Hla-A2 and Hla-A3 constructed by invivo recombination allow mapping of Hla-A2 and Hla-A3 140: 2422-2430

Stamatakis, K., et al., Isoprenylation of RhoB is necessary for its degradation. A novel determinant in the complex regulation of RhoB expression by the mevalonate pathway. J. Biol. Chem 2002, 277:49389

Walter E A, Greenberg P D, Gilbert M J, Finch R J, Watanabe K S, Thomas E D, Riddell S R. Reconstitution of cellular immunity against cytomegalovirus in recipients of allogeneic bone marrow by transfer of T-cell clones from the donor. N Engl J Med 1995; %19; 333(16):1038-1044.

The invention claimed is:

1. A method of treating a metastatic cancer disease, the method comprising administering to a patient suffering from a metastatic cancer disease, an effective amount of an isolated immunologically active peptide fragment from RhoC of SEQ ID NO:1 consisting of 18 to 25 consecutive amino acids, 8 to 10 consecutive amino acids, or 26 to 60 consecutive amino acids, wherein at the most two amino acids have been substituted, wherein the peptide fragment contains at least one of amino acid residues I43, Q123, R140, S141, S152, L157, E165, G178, V181, K183, N184, R186, R187, R188, P191 or I192 of RhoC of SEQ ID NO:1, and wherein RhoC is expressed in the metastatic cancer disease.

2. A method of controlling the growth of metastasis in a patient comprising administering to a patient suffering from a cancer expressing RhoC, an effective amount of an isolated immunologically active peptide fragment from RhoC of SEQ ID NO:1 consisting of
- 18 to 25 consecutive amino acids,
- 8 to 10 consecutive amino acids, or
- 26 to 60 consecutive amino acids,
  wherein at the most two amino acids have been substituted, wherein the peptide fragment contains at least one of amino acid residues I43, Q123, R140, S141, S152, L157, E165, G178, V181, K183, N184, R186, R187, R188, P191 or I192 of RhoC of SEQ ID NO:1.

3. The method according to claim 1 or claim 2, which is combined with a further cancer treatment.

4. The method according to claim 1 or claim 2, wherein the further treatment is selected from the group consisting of chemotherapy, radiotheraphy, treatment with immunostimulating substances, gene therapy, treatment with antibodies and treatment using dendritic cells.

5. The method according to claim 1 or claim 2, wherein said peptide fragment comprises the amino acid sequence RXGLQVRKNK of SEQ ID NO: 178, wherein X is selected from the group consisting of alanine and leucine.

6. The method according to claim 1 or claim 2, wherein said peptide fragment comprises the 20 most C-terminal peptides of RhoC ATRAGLQVRKNKRRRGCPIL of SEQ ID NO: 4.

7. The method according to claim 1 or claim 2, wherein said peptide fragment consists of a sequence selected from the group consisting of RAGLQVRKNK of SEQ ID NO: 10, RLGLQVRKNK of SEQ ID NO: 11 and ATRAGLQVRKNKRRRGCPIL of SEQ ID NO: 4.

8. The method according to claim 1 or claim 2, wherein said peptide fragment consists of a sequence selected from the group consisting of RAGLQVRKNK of SEQ ID NO: 10 or RLGLQVRKNK of SEQ ID NO: 11.

9. The method according to claim 1 or claim 2, wherein said peptide fragment consists of the sequence ATRAGLQVRKNKRRRGCPIL of SEQ ID NO: 4 or RAGLQVRKNK of SEQ ID NO: 10.

10. The method according to claim 1 or claim 2, wherein at least one amino acid of RhoC of SEQ ID NO:1 has been substituted, deleted or added within said peptide fragment.

11. The method according to claim 1 or claim 2, wherein an adjuvant is further administered to said patient.

12. The method according to claim 11, wherein the adjuvant is selected from the group consisting of bacterial DNA based adjuvant, oil/surfactant based adjuvant, viral dsRNA based adjuvant, and imidazochinilines.

13. The method according to claim 11, wherein said adjuvant is Montanide ISA adjuvant.

14. The method according to claim 11, wherein the adjuvant is Montanide ISA adjuvant ISA 51 or Montanide ISA 720.

15. The method according to claim 11, wherein the adjuvant is GM-CSF.

* * * * *